US009433670B2

(12) United States Patent
Hoerr et al.

(10) Patent No.: US 9,433,670 B2
(45) Date of Patent: *Sep. 6, 2016

(54) APPLICATION OF MRNA FOR USE AS A THERAPEUTIC AGAINST TUMOUR DISEASES

(71) Applicant: CureVac AG, Tübingen (DE)

(72) Inventors: Ingmar Hoerr, Tübingen (DE); Florian Von Der Mülbe, Stuttgart (DE); Steve Pascolo, Tübingen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/965,551

(22) Filed: Dec. 10, 2015

(65) Prior Publication Data

US 2016/0089426 A1    Mar. 31, 2016

Related U.S. Application Data

(60) Continuation of application No. 14/840,305, filed on Aug. 31, 2015, which is a continuation of application No. 14/325,850, filed on Jul. 8, 2014, now Pat. No. 9,155,788, which is a division of application No. 13/106,548, filed on May 12, 2011, now abandoned, which is a division of application No. 10/870,110, filed on Jun. 18, 2004, now Pat. No. 8,217,016, which is a continuation of application No. PCT/EP02/14577, filed on Dec. 19, 2002.

(30) Foreign Application Priority Data

Dec. 19, 2001 (DE) .................................. 101 62 480

(51) Int. Cl.
| | | |
|---|---|---|
| *A61K 39/00* | (2006.01) | |
| *A61K 38/19* | (2006.01) | |
| *A61K 9/00* | (2006.01) | |
| *A61K 48/00* | (2006.01) | |

(52) U.S. Cl.
CPC ......... *A61K 39/0011* (2013.01); *A61K 9/0021* (2013.01); *A61K 38/193* (2013.01); *A61K 48/00* (2013.01); *A61K 2039/53* (2013.01); *A61K 2039/54* (2013.01); *A61K 2039/55522* (2013.01); *A61K 2039/572* (2013.01); *A61K 2039/70* (2013.01)

(58) Field of Classification Search
CPC ........... A61K 39/0011; A61K 38/193; A61K 2039/53
See application file for complete search history.

(56) References Cited

U.S. PATENT DOCUMENTS

| | | |
|---|---|---|
| 3,906,092 A | 9/1975 | Hilleman et al. |
| 4,373,071 A | 2/1983 | Itakura |
| 4,401,796 A | 8/1983 | Itakura |
| 4,415,732 A | 11/1983 | Caruthers et al. |
| 4,458,066 A | 7/1984 | Caruthers et al. |
| 4,500,707 A | 2/1985 | Caruthers et al. |
| 4,588,585 A | 5/1986 | Mark et al. |
| 4,668,777 A | 5/1987 | Caruthers et al. |
| 4,737,462 A | 4/1988 | Mark et al. |
| 4,816,567 A | 3/1989 | Cabilly et al. |
| 4,879,111 A | 11/1989 | Chong |
| 4,959,314 A | 9/1990 | Mark et al. |
| 4,973,679 A | 11/1990 | Caruthers et al. |
| 5,017,691 A | 5/1991 | Lee et al. |
| 5,047,524 A | 9/1991 | Andrus et al. |
| 5,116,943 A | 5/1992 | Koths et al. |
| 5,132,418 A | 7/1992 | Caruthers et al. |
| 5,153,319 A | 10/1992 | Caruthers et al. |
| 5,262,530 A | 11/1993 | Andrus et al. |
| 5,580,859 A | 12/1996 | Felgner et al. |
| 5,663,153 A | 9/1997 | Hutcherson et al. |
| 5,700,642 A | 12/1997 | Monforte et al. |
| 5,928,649 A | 7/1999 | Daley |
| 5,965,720 A | 10/1999 | Gryaznov et al. |
| 5,965,726 A | 10/1999 | Pavlakis et al. |
| 6,214,804 B1 | 4/2001 | Felgner et al. |
| 6,239,116 B1 | 5/2001 | Krieg et al. |
| 6,265,387 B1 | 7/2001 | Wolff et al. |
| 6,322,967 B1 | 11/2001 | Parkin |
| 6,376,248 B1 | 4/2002 | Hawley-Nelson et al. |
| 6,406,705 B1 | 6/2002 | Davis et al. |

(Continued)

FOREIGN PATENT DOCUMENTS

| | | |
|---|---|---|
| CA | 2376634 | 12/2000 |
| CA | 2473135 | 6/2003 |

(Continued)

OTHER PUBLICATIONS

Hoerr et al. (Eur. Jo. Immunol. 2000; 30:1-7).*
Sypniewska et al (Breast Cancer Research and Treatment. Aug. 2002; 74: 221-233).*
Akashi, "Gene expression and molecular evolution," *Curr. Opin. Genet. Dev.*, 11 (6):660-666, 2001.
Alberts et al., Molecular biology of the Cell, 3rd ed. Garland Publishing, Inc. New York, NY, pp. 368-369, 1994.
Altschul et al., "Gapped BLAST and PSI-BLAST: a new generation of protein database search programs," *Nucleic Acids Res*, 25(17): 3389-3402, 1997.
Anichini et al., "Cylotoxic T cells directed to tumor antigens not expressed on normal melanocytes dominate HLA-A2.1-restricted immune repertoire to melanoma," *J Immunol.*, 156(1): 208-217, 1996.

(Continued)

*Primary Examiner* — Scott Long
(74) *Attorney, Agent, or Firm* — Parker Highlander PLLC

(57) ABSTRACT

The present invention relates to a pharmaceutical composition comprising at least one mRNA comprising at least one coding region for at least one antigen from a tumor, in combination with an aqueous solvent and preferably a cytokine, e.g. GM-CSF, and a process for the preparation of the pharmaceutical composition. The pharmaceutical composition according to the invention is used in particular for therapy and/or prophylaxis against cancer.

20 Claims, 14 Drawing Sheets

(56) References Cited

U.S. PATENT DOCUMENTS

| | | | |
|---|---|---|---|
| 6,500,919 | B1 | 12/2002 | Adema et al. |
| 6,514,948 | B1 | 2/2003 | Raz et al. |
| 6,552,006 | B2 | 4/2003 | Raz et al. |
| 6,589,940 | B1 | 7/2003 | Raz et al. |
| 6,610,661 | B1 | 8/2003 | Carson et al. |
| 6,664,066 | B2 | 12/2003 | Parks |
| 6,924,365 | B1 | 8/2005 | Miller et al. |
| 7,001,890 | B1 | 2/2006 | Wagner et al. |
| 7,208,478 | B2 | 4/2007 | Carson et al. |
| 7,268,120 | B1 | 9/2007 | Horton et al. |
| 7,276,489 | B2 | 10/2007 | Agrawal et al. |
| 7,316,925 | B2 | 1/2008 | Draghia-Akli et al. |
| 9,155,788 | B2 * | 10/2015 | Hoerr ................... A61K 38/193 |
| 2002/0123099 | A1 | 9/2002 | Weiner et al. |
| 2002/0132788 | A1 | 9/2002 | Lewis et al. |
| 2003/0077604 | A1 * | 4/2003 | Sun ........................ C07K 14/47 435/6.16 |
| 2003/0143204 | A1 | 7/2003 | Lewis et al. |
| 2003/0143743 | A1 | 7/2003 | Schuler et al. |
| 2003/0170273 | A1 | 9/2003 | O'hagan et al. |
| 2003/0225016 | A1 | 12/2003 | Fearon et al. |
| 2004/0005667 | A1 | 1/2004 | Ratti et al. |
| 2004/0106567 | A1 | 6/2004 | Hagstrom et al. |
| 2005/0032730 | A1 | 2/2005 | Von der Mulbe et al. |
| 2005/0037494 | A1 | 2/2005 | Hecker et al. |
| 2005/0059624 | A1 | 3/2005 | Hoerr et al. |
| 2005/0064596 | A1 | 3/2005 | Riemen et al. |
| 2005/0112141 | A1 | 5/2005 | Terman |
| 2005/0250723 | A1 | 11/2005 | Hoerr et al. |
| 2006/0172966 | A1 | 8/2006 | Lipford et al. |
| 2006/0188490 | A1 | 8/2006 | Hoerr et al. |
| 2006/0241076 | A1 | 10/2006 | Uhlmann et al. |
| 2008/0025944 | A1 | 1/2008 | Hoerr et al. |
| 2008/0171711 | A1 | 7/2008 | Hoerr et al. |

FOREIGN PATENT DOCUMENTS

| | | |
|---|---|---|
| CA | 2480775 | 10/2003 |
| DE | 10119005 | 4/2001 |
| DE | 10229872 | 1/2004 |
| EP | 0839912 | 5/1998 |
| EP | 1083232 | 3/2001 |
| EP | 1393745 | 3/2004 |
| EP | 1604688 | 12/2005 |
| WO | WO 90/11092 | 10/1990 |
| WO | WO 93/14778 | 8/1993 |
| WO | WO 95/24485 | 9/1995 |
| WO | WO 95/26204 | 10/1995 |
| WO | WO 97/41210 | 11/1997 |
| WO | WO 97/48370 | 12/1997 |
| WO | WO 98/12207 | 3/1998 |
| WO | WO 98/34640 | 8/1998 |
| WO | WO 98/55495 | 12/1998 |
| WO | WO 99/14346 | 3/1999 |
| WO | WO 99/20774 | 4/1999 |
| WO | WO 99/52503 | 10/1999 |
| WO | WO 00/29561 | 5/2000 |
| WO | WO 00/75304 | 12/2000 |
| WO | WO 01/04313 | 1/2001 |
| WO | WO 01/21810 | 3/2001 |
| WO | WO 01/93902 | 12/2001 |
| WO | WO 02/08435 | 1/2002 |
| WO | WO 02/064799 | 8/2002 |
| WO | WO 02/098443 | 12/2002 |
| WO | WO 03/028656 | 4/2003 |
| WO | WO 03/051401 | 6/2003 |
| WO | WO 03/059381 | 7/2003 |
| WO | WO 03/066649 | 8/2003 |
| WO | WO 03/086280 | 10/2003 |
| WO | WO 2004/058159 | 7/2004 |
| WO | WO 2004/092329 | 10/2004 |
| WO | WO 2006/008154 | 1/2006 |
| WO | WO 2006/024518 | 3/2006 |
| WO | WO 2007/024708 | 3/2007 |

OTHER PUBLICATIONS

Apostolopoulos et al., "Cellular mucins: targets for immunotherapy," *Crit Rev Immunol.*, 14(3-4):293-309, 1994.

Ashley et al., "Bone marrow-generated dendritic cells pulsed with tumor extracts or tumor RNA induce antitumor immunity against central nervous system tumors," *J Exp Med*, 186(7): 1177-1182, 1997.

Aurup et al., "Translation of 2'-modified RNA in vitro and in vivo," *Nucleic Acids Research*, 22(2:3):4963-4968, 1994.

Austyn et al., "New insights into the mobilization and phagocytic activity of dendritic cells," *J Exp Med*, 183(4):1287-1292, 1996.

Berneman et al., "T-Cell Stimulatory Capacity of Different Types of In Vitro Cultured Monocyte-Derived Dendritic Cells Following Electroporation with RNA Encoding Defined Antigens," Laboratory of Experimental Hematology, University of Antwerp, 1(11), Abstract No. 5536, Nov. 16, 2002.

Bernhard et al., "Generation of immunostimulatory dendritic cells from human CD34+ hematopoietic progenitor cells of the bone marrow and peripheral blood," *Cancer Res*, 55(5): 1099-1104, 1995.

Bettinger et al., "Peptide-mediated RNA delivery: a novel approach for enhanced transfection of primary and post-mitotic cells," *Nucleic Acids Research*, 29(18):3882-3891, 2001.

Bevan, "Antigen presentation to cytotoxic T lymphocytes in vivo," *J Exp Med*, 182(3):639-641, 1995.

Bevilacqua et al., "Post-transcriptional regulation of gene expression by degradation of messenger RNAs," *Journal of Cellular Physiology*, 195(31):356-372, 2003.

Bieler und Wagner (in: Schleef), Plasmids for Therapy and Vaccination, Kapitel 9, Seiten 147-168, Wiley-VCH, Weinheim, 2001.

Binder et al., "Evidence that the pathway of transferrin receptor mRNA degradation involves and endonucleolytic cleavage within the 3' UTR and does not involve poly (A) tail shortening," *EMBO J.*, 13(8):1969-1980, 1994.

Bocchia et al., "Antitumor vaccination: where we stand," *Hematologica*, 85(11):1172-1206, 2000.

Boczkowski et al., "Dendritic cells pulsed with RNA are potent antigen-presenting cells in vitro and in vivo," *J. Exp. Med.*, 184:465-472, 1996.

Boczkowski et al., "Induction of tumor immunity and cytotoxic T lymphocyte responses using dendritic cells transfected with messenger RNA amplified from tumor cells," *Cancer Res.*, 60(4):1028-1034, 2000.

Boon et al., "Genes coding for tumor rejection antigens: perspectives for specific immunotherapy,"*Important Adv Oncol*, 53-69, 1994.

Boyum, "Separation of White Blood Cells," *Nature*, 204:793-794, 1964.

Brandt et al., "Detection of the metastatic potential of blood-borne and immunomagnetically enriched epithelial cells by quantitative erbB-2 RT-PCR," *Clin. Exp. Metastasis*, 14:399-408, 1996.

Brossart et al., "Her-2/neu-derived peptides are tumor-associated antigens expressed by human renal cell and colon carcinoma lines and are recognized by in vitro induced specific cytotoxic T lymphocytes," *Cancer Res*, 58(4):732-736, 1998.

Brossait et al., "Identification of HLA-A2-restricted T-cell epitopes derived from the MUCI tumor antigen for broadly applicable vaccine therapies," Blood, 93(12):4309-4317, 1999.

Brossart et al., "Induction of cytotoxic T-lymphocyte responses in vivo after vaccinations with peptide-pulsed dendritic cells," *Blood*, 96(9):3102-3108, 2000.

Brossart et al., "Virus-mediated delivery of antigen ic epitopes into dendritic cells as a means to induce CTL." *J Immunol,*, 158(7):3270-3276, 1997.

Cannon et al., "RNA Based Vaccines," *DNA and Cell Biology*, 21(12): 953-961, 2002.

Caput et al., "Identification of a common nucleotide sequence in the 3'-untranslated region of mRNA molecules specifying; inflammatory mediators," *Proc. Natl. Acad. Sci. USA*, 83:1670-1674, 1986.

Carralot et al., "Polarization of immunity induced by direct injection of naked sequence-stabilized mRNA vaccines," *Cell Mol Life Sci*, 61(18): 2418-2424, 2004.

(56) References Cited

OTHER PUBLICATIONS

Carralot et al., "Production and characterization of amplified tumor-derived cRNA libraries to be used as vaccines against metastatic melanomas" *Genetic Vaccines and Therapy*, 3(6):1-10, 2005.
CD154, Wikipedia, the free encyclopedia, Jun. 25, 2010.
Celluzzi et al., "Peptide-pulsed dendritic cells induce antigen-specific CTL-mediated protective immunity," *J Exp Med*, 183(1):283-287, 1996.
Chen et al., "Enhanced protection against a lethal influenza virus challenge by immunization with both hemagglutinin- and neuraminidase-expressing DNAs," *Vaccine*, 17(7-8): 653-659, 1999.
Cheng et al., "Enhancement of Sindbis virus self-replicating RNA vaccine potency by linkage of *Mycobacterium tuberculosis* heat shock protein 70 gene to an antigen gene," *Journal of Immunology*, 166(10):6218-6226, 2001.
Cheng et al., "Enhancement of Sindbis virus self-replicating RNA vaccine potency by linkage Herpes simplex virus type I VP22 protein to antigen," *J. Virol.*, 75(5):2368-2376, 2001.
Cho et al., "Enhanced cellular immunity to hepatitis C virus nonstructural proteins by codelivery of granulocyte macrophage-colony stimulating factor gene in intramuscular DNA immunization," *Vaccine*, 17(9-10):1136-1144, 1999.
Cohen et al., "Murine epidermal Langerhans cells and splenic dendritic cells present tumor-associated antigens to primed T cells," *Eur J Immunol*, 24(2):315-319, 1994.
Conroy et al., "Characterization of a messenger RNA polynucleotide vaccine vector," *Cancer Research*, 55(7):1397-1400, 1995.
Coughlin et al., "Targeting adult and pediatric cancers via cell-based vaccines and the prospect of activated B lymphocytes as a novel modality," *Cancer Biology & Therapy*, 2(5):466-470, 2003.
Cramer et al., "Functional association between promoter structure and transcript alternative splicing," *PNAS*, 94(21):11456-11460, 1997.
Culver et al., Gene Therapy, A Handbook for Physicians, pp. 63-77, 1994.
Database Corenucleotide, NCBI Database accession No. AF033819, Aug. 2002.
Database Geneseq, Database accession No. AAV21762, Jul. 1998.
Deres et al., "In vivo priming of virus-specific cytotoxic T lymphocytes with synthetic lipopeptide vaccine," *Nature*, 342:561-564, 1989.
Deshayes et al., "Cell-penetrating peptides: tools for intracellular delivery of therapeutics," *Cell Mol Life Sci*, 62(16):1839-1849, 2005.
Diebold et al., "Innate antiviral responses by means a TLR7-mediated recognition of single-stranded RNA," *Science*, 303(5663):1529-1531, 2004.
Disbrow et al., "Codon optimization of thee HPV-16 E5 gene enhances protein expression," *Virology*, 311:105-114, 2003.
Donnelly et al., "Technical and regulatory hurdles for DNA vaccines," *Int J Parasitol*, 33(5-6):457-467, 2003.
Dunham et al., "The application of nucleic acid vaccines in veterinary medicine," *Research in Veterinary Science*, 73:9-16, 2002.
Duret et al., "Expression pattern and, surprisingly, gene length shape codon usage in Caenorhabditis, *Drosophila*, and Arabidopsis," *Proc. Nat. Acad. Sci. USA*, 96:4482-4487, 1999.
Edelstein et al., "Gene therapy clinical trials worldwide 1989-2004—an overview," *J. Gene Med.*, 6(6):597-602, 2004.
Egeter et al., "Eradication of Disseminated Lymphomas with CpG-DNA Activated T Helper Type 1 Cells from Nontransgenic Mice," *Cancer Research*, 60(6):1515-1520, 2000.
Elbashir et al., "Duplexes of 21-nucleotide RNAs mediate RNA interference in cultured mammalian cells," *Nature*, 411(6836):494-498, 2001.
Fang et al., "Functional Measurement of Hepatitis C Virus Core-Specific CD8+ T-Cell Responses in the Livers or Peripheral Blood of Patients by Using Autologous Peripheral Blood Mononuclear Cells as Targets or Stimulators," *Journal of Clinical Microbiology*, 39(11):3985-3901, 2001.
Fearnley et al., "Monitoring human blood dendritic cell numbers in normal individuals and in stem cell transplantation," *Blood*, 93(2):728-736, 1999.
Finn et al., "MUC-1 epithelial tumor mucin-based immunity and cancer vaccines," *Immunological Reviews*, 145:61-89, 1995.
Fisch et al., "Generation of antigen-presenting cells for soluble protein antigens ex vivo from peripheral blood CD34+ hematopoietic progenitor cells in cancer patients," *Eur J Immunol*, 26(3):595-600, 1996.
Fisk et al., "Identification of an immunodominant peptide of HER-2/neu protooncogene recognized by ovarian tumor-specific cytotoxic T lymphocyte lines," *J Exp Med*, 181(6):2109-2117, 1995.
Ford et al., "The poly(A) tail inhibits the assembly of a 3'-to-5' exonuclease in an in vitro RNA stability system," *Molecular and Cellular Biology*, 17(1):398-406, 1997.
Fynan et al., "DNA vaccines: protective immunizations by parenteral, mucosal, and gene-gun inoculations," *Proc Natl Acad Sci USA*, 90(24):11478-11482, 1993.
Gao et al., "Nonviral gene delivery: what we know and what is next," *AAPS J*, 9(1):E92-E104, 2007.
Garbe et al., "[Epidemiology of malignant melanoma in West Germany in an international comparison]," Onkologie 12(6): 253-62, 1989. [Article in German].
GenBank: U26404, 1996, and Lai et al., "Patterning of the neural ectoderm of Xenoptis laevis by the amino-terminal product of hedgehog autoproteolytic cleavage," *Development*, 121(8):2349-2360, 1995.
GenBank: X65300, 1999, "Cloning vector pGEM-1," Technical Services, Promega Corporation, May 28, 1993.
GenBank: X65327, 1999, "Cloning vector pSP64," Technical Services, Promega Corporation, Mar. 23, 1992.
Gilewski et al., "Vaccination of high-risk breast cancer patients with mucin-1 (MUC1) keyhole limpet hemocyanin conjugate plus QS-21," *Clin Cancer Res.*, 6(5):1693-1701, 2000.
Gilkeson et al., "Induction of cross-reactive anti-dsDNA antibodies in preautoimmune NZB/NZW mice by immunization with bacterial DNA," *J Clin Invest*, 95(3):1398-1402, 1995.
Grabbe et al., "Dendritic cells as initiators of tumor immune responses: a possible strategy for tumor immunotherapy?"*Immunol Today*, 16(3):117-121, 1995.
Grabbe et al., "Tumor antigen presentation by epidermal antigen-presenting cells in the mouse: modulation by granulocyte-macrophage colony-stimulating factor, tumor necrosis factor alpha, and ultraviolet radiation," *J Leukoc Biol*, 52(2):209-217, 1992.
Grabbe et al., "Tumor antigen presentation by murine epidermal cells," *J Immunol*, 146(10):3656-3661, 1991.
Graham et al., "Intramuscular immunization with MUC1 cDNA can protect C57 mice challenged with MUC1-expressing syngeneic mouse tumor cells," *International Journal of Cancer*, 65:664-670, 1996.
Gram et al., "Immunological analysis of a Lactococcus lactis-based DNA vaccine expressing HIV gp120," *Genetic Vaccine and Therapy*, 5:3, 2007.
Granstein et al., "Induction of anti-tumor immunity with epidermal cells pulsed with tumor-derived RNA or intradermal administration of RNA," *J Invest Dermatol.*, 114(4):632-636, 2000.
Gryaznov, "Oligonucleotide N3'->P5' phosphoramidates as potential therapeutic agents," *Biochim Biophys Acta.*, 1489(1):131440, 1999.
Haas et al., "Codon usage limitation in the expression of HIV-1 envelope glycoprotein," *Current Biology*, 6(3):315-324, 1996.
Havranek et al., "Advances in prostate cancer immunotherapy," *Surgical Oncology*, 11(1-2):35-45, 2002.
Heidenreich et al., "Chemically modified RNA: approaches and applications," *FASEB Journal*, 7(1):90-96, 1993.
Heil et al., "Species-specific recognition of single-stranded RNA via toll-like receptor 7 and 8," *Science*; 303(5663):1526-4529, 2004.

(56) References Cited

OTHER PUBLICATIONS

Heiser et al., "Autologous dendritic cells transfected with prostate-specific antigen RNA stimulate CTL responses against metastatic prostate tumors," *Journal of Clinical Investigation*, 109(3):409-417, 2002.
Heiser et al., "Human dendritic cells transfected with renal tumor RNA stimulate polyclonal T-cell responses against antigens expressed by primary and metastatic tumors," *Cancer Research*, 61(8):3388-3393, 2001.
Heiser et al., "Human dendritic cells transfected with RNA encoding prostate-specific antigen stimulate prostate-specific CTL responses in vitro," *Journal of Immunology*, 164(10):5508-5514, 2000.
Heiser et al., "Induction of polyclonal prostate cancer-specific CTL using dendritic dells transfected with amplified tumor RNA," *J. Immunol.*, 166(5):2953-2960, 2001.
Hemmi et al., "A toll-like receptor recognizes bacterial DNA," *Nature*, 408:740-745, 2000.
Herweijer et al., "Gene therapy progress and prospects: Hydrodynamic gene delivery," *Gene Ther.*, 14(2):99-107, 2007.
Hilleren et al., "Mechanisms of mRNA surveillance in eukaryotes," *Annu Rev Genet.*, 3:229-260, 1999.
Hirasawa, "Natural autoantibody to MUC1 a prognostic indicator for non-small cell lung Cancer," *American Journal of Respiratoty and Critical Care Medicine*, 161:589-594, 2000.
Hoath et al., "The Organization of Human Epidermis: Functional Epidennal Units and Phi Proportionality," *J. Invest. Dermatol.*, 121:1440-1446, 2003.
Hoerr et al., "In vivo application of RNA leads to induction of specific cytotoxic T lymphocytes and antibodies," *Eur. J. Immunol.*, 30(1):1-7, 2000.
Holcik et al., "Four highly stable eukaryotic mRNAs assemble 3' untranslated region RNA-protein complexes sharing cis and trans components," *Proc Natl Acad Sci USA*, 94(6):2410-2414, 1997.
Holmes and Morgan, "Cell positioning and sorting using dielectrophoresis," *European Cells and Materials*, 4(Suppl. 2):120-122, 2002.
Houghton, "Cancer antigens: immune recognition of self and altered self," *J Exp Med*, 180(1):1-4, 1994.
Hsu et al., "Vaccination of patients with B-Cell lymphoma using autologous antigen-pulsed dendritic cells," *Nat Med*, 2(1):52-58, 1996.
Huddleston et al., "The sequence of the nucleoprotein gene of human influenza A virus, strain A/NT/60/68," *Nucleic Acids Research*, 10(3):1029-1038, 1982.
Inaba et al., "Dendritic cells pulsed with protein antigens in vitro can prime antigen-specific, MHC-restricted T cells in situ," *J Exp Med*, 172(2):631-640, 1990.
Inaba et al., "Direct activation of CD8+ cytotoxic T lymphocytes by dendritic cells." *J Exp Med*, 166(1):182-194, 1987.
Iwasaki et al., "Enhanced CTL responses mediated by plasmid DNA immunogens encoding costimulatory molecules and cytokines," *J Immunol*, 158(10):4591-4601, 1997.
Janeway et al., Immunobiology, The Immune System in Health and Disease, 13:12-13:21, 1997.
Janssens et al., "Role of Toll-Like Receptors in Pathogen Recognition," *Clinical Microbiology Reviews*, 16(4):637-646, 2003.
Januszyk and Lima, "Stuctural components and architectures of RNA exosomes," in: Madame Curie Bioscience Database (Internet), Austin (TX), Landes Bioscience, available from: http://www.ncbi.nlm.nih.gov/books/NBK45033/, printed as pp. 1-19, 2000.
Kabanov et al., "A new class of antivirals: antisense oligonucleotides combined with a hydrophobic substituent effectively inhibit influenza virus reproduction and synthesis of virus-specific proteins in MDCK cells," *FEBS Lett*, 259(2): 327-330, 1990.
Kalnins et al., "Sequence of the lacZ gene of *Escherichia coli*," *EBMO J.*, 2(4): 593-597, 1983.
Kandimalla et al., "Divergent synthetic nucleotide motif recognition pattern: design and development of potent immunomodulatory oligodeoxyribonucleotide agents with distinct cytokine induction profiles," *Nucleic Acids Research*, 31(9):2393-2400, 2003.
Kandimallia et al., "Immunomodulatory oligonucleotides containing a cytosine-phosphate-2'-deoxy-7-deazaguanosine motif as potent toll-like receptor 9 agonists," *PNAS*, 102(19):6925-6930, 2005.
Kariko et al., "Suppression of RNA Recognition by Toll-like Receptors: The Impact of Nucleoside Modification and the Evolutionary Origin of RNA," *Immunity*, 23:165-175, 2005.
Karlin et al., "Applications and statistics for multiple high-scoring segments in molecular sequences," *Proc Natl Acad Sci USA*, 90(12): 5873-5877, 1993.
Kim et al., "Codon optimization for high-level expression of human erythropoietin (EPO) in mammalian cells," *Gene*, 199:293-301, 1997.
Klinman et al., "DNA vaccines: safety and efficacy issues" *Springer Semin Immunopathol*, 19(21):245-256, 1997.
Kohler et al., "Continuous cultures of fused cells secreting antibody of predefined specificity," *Nature*, 256(5517):495-497, 1975.
Koide et al., "DNA Vaccines," *Jpn J. Pharmacol.*, 83(3):167-174, 2000.
Koido et al., "Induction of antitumor immunity by vaccination of dendritic cells transfected with MUC1 RNA," , *J Immunol*, 165(10):5713-5719, 2000.
Komar et al., "Synonymous codon substitutions affect ribosome traffic and protein folding during in vitro translation," *FEBS Letters*, 462:387-391, 1999.
Kontermann, "Recombinant bispecific antibodies for cancer therapy," *Acta Pharmacol Sin*, 26(1):1-9, 2005.
Krieg et al., "In vitro RNA synthesis with SP6 RNA polymerase," *Methods Enzymol*, 155:397-415, 1987.
Kudla et al., "High Guanine and Cytosine Content Increases mRNA Levels in Mammalian Cells," *PLoS Biol*, 4(6):e180, 2006.
Kufe et al., Cancer Medicine, 6th edition, Table 12-1, 2003.
Kugler et al., "Regression of human metastatic renal cell carcinoma after vaccination with tumor cell-dendritic cell hybrids," *Nat Med*, 6(3):332-336, 2000.
Kusakabe et al., "The timing of GM-CSF expression plasmid administration influences the Th1/Th2 response induced by an HIV-1-specific DNA vaccine," *J Immunol*, 164(6): 3102-3111, 2000.
Kwissa et al., "Cytokine-facilitated priming of CD8+ cell responses by DNA vaccination," *J Mol Med (Berl)*, 81(2):91-101, 2003.
Larregina et al., "Changing Paradigms in Cutaneous Immunology: Adapting with Dendritic Cells," *The Journal of Investigative Dermatology*, 124(1):1-12, 2005.
Lathe, "Synthetic oligonticleotide probes deduced from amino acid sequence data. Theoretical and practical considerations," *Journal of Molecular Biology*, 183(1)1-12, 1985.
Lee et al., "Molecular basis for the immunostimulatory activity of guanine nucleoside analogs: Activation of Toll-like receptor 7," *PNAS*, 100(11):6646-6651, 2003.
Leitner et al, "DNA and RNA-based vaccines: principles, progress and prospects," *Vaccine*, 18:765-777, 1999.
Lenz et al., "Human and murine dermis contain dendritic cells. Isolation by means of a novel method and phenotypical and functional characterization," *Journal of Clinical Investigation*, 92:2587-2596, 1993.
Linehan et al., "Tumor-specific and HLA-A2-restricted cytolysis by tumor-associated lymphocytes in human metastatic breast cancer," *J Immunol*, 155(9):4486-4491, 1995.
Loging et al., "Identifying potential tumor markers and antigens by database mining and rapid expression screening" *Genome Res.*, 10:1393-1402, 2000.
Luo et al., "Synthetic DNA delivery systems," *Nature Biotechnology*, 18:33-37, 2000.
Martinon et al., "Induction of virus-specific cytotoxic T lymphocytes in vivo by liposome-entrapped. mRNA," *Eur J Immunol*, 23(7): 1719-1722, 1993.
Mathers et al., "Professional antigen-presenting cells of the skin," *Immunol Res*, 36(1-3):127-136, 2006.

(56) References Cited

OTHER PUBLICATIONS

Matray et al., "Synthesis and properties of RNA analogs—oligoribonucleotide N3'→ P5' phosphoramidates," *Nucleic Acids Research*, 27(20):3976-3985, 1999.
McCafferty et al., "Phage: antibodies: filamentous phage displaying antibody variable domains," *Nature*, 348(6301):552-554, 1990.
McKenzie et al., "Nucleic acid vaccines: tasks and tactics," *Immunologic Research*, 24(3):225-244, 2001.
Meunier et al., "Heterogeneous populations of class II MHC+ cells in human dermal cell suspensions. Identification of a small subset responsible for potent dermal antigen-presenting cell activity with features analogous to Langerhans cells," *The Journal of Immunology*, 151(8):4067-4080, 1993.
Minks et al., "Structural Requirements of Double-stranded RNA for the Activation of 2',5'—oligo(A) Polymerase and Protein Kinase of Interferon-treated HeLa Cells," *The Journal of Biological Chemistry*, 254(20):10180-10183, 1979.
Mishra et al., "Improved leishmanicidal effect of phosphorotioate antisense oligonucleotides by LDL-mediated delivery," *Biochim Biophys Acta*, 1264(2):229-237, 1995.
Mitchell et al., "RNA transfected dendritic cells as cancer vaccines," *Curr. Opin. Mol. Ther.*, 2(2):176-181, 2000.
Mitchell et al., "RNA-transfected dendritic cells in cancer immunotherapy." *J Clin Invest*, 106(9):1065-1069, 2000.
Mitchell, "MRNA turnover,"*Curr Opin Cell Biol.*, 13(3):320-325, 2001.
Morinaga et al., "Primary structures of human α-fetoprotein and its mRNA," *PNAS*, 80:4604-4608, 1983.
Morse et al., "Generation of dendritic cells in vitro from peripheral blood mononuclear cells with granulocyte-macrophage-colony-stimulating factor, interleukin-4, and tumor necrosis factor-alpha for use in cancer immunotherapy," *Annals of Surgery*, 226:6-16, 1997.
Müller et al., "Transfection of dendritic cells with RNA induces CD4- and CD8-mediated T cell immunity against breast carcinomas and reveals the immunodominance of presented T cell epitopes," *J Immunol*, 170(12):5892-5896, 2003.
Nagata et al., "Codon optimization effect on translational efficiency of DNA vaccine in Mammalian cells: Analysis of plasmid DNA encoding a CTL epitope derived from microorganisms," *Biochemical and Biophysical Research Communications*, 261:445-451, 1999.
Nair et al., "Antigen-presenting cells pulsed with unfractionated tumor-derived peptides are potent tumor vaccines," *Eur J Immunol*, 27(3):589-597, 1997.
Nair et al., "Induction of cytotoxic T cell responses and tumor immunity against unrelated tumors using telomerase reverse transcriptase RNA transfected dendritic cells," *Nat Med*, 6(9):1011-1017, 2000.
Nair et al., "Induction of primaiy carcinoembryonic antigen (CEA)-specific cytotoxic T lymphocytes in vitro using human dendritic cells transfected with RNA," *Nat Biotechnol*, 16(4):364-369, 1998.
Nair et al., "Soluble proteins delivered to dendritic cells via pH-sensitive liposomes induce primary cytotoxic T lymphocyte responses in vitro" *J Exp Med*, 175(2):609-612, 1992.
Nestle et al., "Vaccination of melanoma patients with peptide- or tumor lysate-pulsed dendritic cells," *Nat Med*, 4(3):328-332, 1998.
Nicholson et al., "Accurate in vitro cleavage by RNase III of phosphorothioate-substituted RNA processing signals in bacteriophage T7 early mRNA," *Nucleic Acids Research*, 16(4):1577-1591, 1988.
O'Doherty et al., "Human blood contains two subsets of dendritic cells, one immunologically mature and the other immature," *Immunology*, 82:487-493, 1994.
Oberhauser et al., "Effective incorporation of 2'-O-methyl-oligoribonucleotides into liposomes and enhanced cell association through modification with thiocholesterol," *Nucleic Acids Res*, 20(3):533-538, 1992.
Office Action issued in U.S. Appl. No. 10/870,110, mailed Dec. 15, 2006.
Office Action issued in U.S. Appl. No. 10/870,110, mailed Dec. 11, 2007.
Office Action issued in U.S. Appl. No. 10/870,110, mailed Jan. 28, 2010.
Office Action issued in U.S. Appl. No. 10/870,110, mailed Jul. 22, 2008.
Office Action issued in U.S. Appl. No. 10/870,110, mailed Jan. 25, 2011.
Office Action issued in U.S. Appl. No. 10/870,110, mailed Jul. 26, 2010.
Office Action issued in U.S. Appl. No. 10/870,110, mailed May 14, 2007.
Office Action issued in U.S. Appl. No. 10/870,110, mailed Mar. 4, 2009.
Office Action issued in U.S. Appl. No. 13/106,548, mailed Apr. 14, 2014.
Office Action issued in U.S. Appl. No. 13/106,548, mailed Apr. 5, 2012.
Office Action issued in U.S. Appl. No. 13/106,548, mailed Dec. 29, 2011.
Office Action issued in U.S. Appl. No. 13/106,548, mailed May 17, 2013.
Office Action issued in U.S. Appl. No. 13/106,548, mailed Nov. 10, 2011.
Office Action issued in U.S. Appl. No. 13/106,548, mailed Oct. 24, 2013.
Office Action issued in U.S. Appl. No. 14/325,850, mailed Nov. 18, 2014.
Office Action issued in U.S. Appl. No. 14/840,305, mailed Feb. 1, 2016.
Office Action issued in U.S. Appl. No. 14/965,340, mailed Jan. 22, 2016.
Office Action issued in U.S. Appl. No. 14/965,485, mailed Jan. 22, 2016.
Paglia et al., "Murine dendritic cells loaded in vitro with soluble protein prime cytotoxic T lymphocytes against tumor antigen in vivo," , *J Exp Med*, 183(1):317-322, 1996.
Palu et al., "In pursuit of new developments for gene therapy of human diseases," *J. Biotechnol.*, 68:1-13, 1999.
Palucka et al., "Taming cancer by inducing immunity via dendritic cells," *Immunological Reviews*, 220:129-150, 2007.
Peoples et al., "Breast and ovarian cancer-specific cytotoxic T lymphocytes recognize the same HER2/neu-derived peptide," *Proc Natl Acad Sci USA*, 92(2):432-436, 1995.
Pesole et al., "UTRdb and UTRsite: specialized databases of sequences and functional elements of 5' and 3' untranslated regions of eukaryotic MRNAs. Update 2002," *Nucleic Acids Res.*, 30(1):335-340, 2002.
Ponsaerts et al., "Cancer immunotherapy using RNA-loaded dendritic cells," *Clinical and Experimental Immunology*, 134:378-384, 2003.
Porgador et al., "Bone marrow-generated dendritic cells pulsed with a class I-restricted peptide are potent inducers of cytotoxic T lymphocytes," *J Exp Med*, 182(1):255-260, 1995.
Porgador et al., "Induction of antitumor immunity using bone marrow-generated dendritic cells," *J Immunol*, 156(8):2918-2926, 1996.
Rajagopalan et al., "Turnover and Translation of in Vitro Synthesized Messenger RNAs in Transfected, Normal Cells," *The Journal of Biological Chemistry*, 271(33):19871-19876, 1996.
Ramazeilles et al., "Antisense phosphorotbioate oligonucleotides: selective killing of the intracellular parasite Leishmania amazonensis," *Proc. Natl. Acad. Sci. USA*, 91:7859-7863, 1994.
Rammensee et al., "Peptides naturally presentee by MHC class I molecules." *Annu Rev Immunol*, 11:213-244, 1993.
Renkvist et al., "A listing of human tumor antigens recognized by T cells," *Cancer Immunol Immunother.*, 50:3-15, 2001.
Reyes-Sandoval et al., "DNA vaccines," *Current Molecular Medicine*, 1(2): 217-243, 2001.
Rittig et al., "Intradermal vaccinations with RNA coding for TAA generate CD8+ and CD4+ immune responses and induce clinical benefit in vaccinated patients," *Mol. Ther.*, 19(5):990-999, 2011.
Robbins et al., "Human tumor antigens recognized by T cells," *Curr Opin Immunol*, 8(5):628-636, 1996.

(56) References Cited

OTHER PUBLICATIONS

Robinson et al., "Expression of Human nPTB is Limited by Extreme Suboptimal Codon Content," *PLoS One*, 3(3): e1801, 2008.
Robinson et al., "Protection against a lethal influenza virus challenge by immunization with a haemagglutinin-expressing plasmid DNA," *Vaccine*, 11(9):957-960, 1993.
Rock, "A new foreign policy: MHC class I molecules monitor the outside world" *Immunol Today*, 17(3):131-137, 1996.
Roitt, Brostoff and Male, Immunology, 4th Edition, Barcelona: Times Mirror International Publishers Limited, p. 1.7, 1996.
Romani et al., "Generation of mature dendritic cells from human blood. An improved method with special regard to clinical applicability," *Journal Immunological Methods*, 196:137-151, 1996.
Romani et al., "Presentation of exogenous protein antigens by dendritic cells to T cell clones. Intact protein is presented best by immature, epidermal Langerhans cells," *J Exp Med*, 169(3):1169-1178, 1989.
Rosenberg et al., "Cancer immunotherapy: moving beyond current vaccines," *Nat. Med*, 10(9):909-915, 2004.
Ross et al., "Control of messenger RNA stability in higher eukaryotes," *Trends Genet.*, 12(5):171-175, 1996.
Saenz-Badillos et al., "RNA as a tumor vaccine: a review of the literature," *Exp. Dermatol.*, 10(3):143-154, 2001.
Saison-Behmoaras et al., "Short modified antisense oligonucleotides directed against Ha-ras point mutation induce selective cleavage of the mRNA and inhibit T24 cells proliferation," *EMBO J*, 10(5):1111-1118, 1991.
Sakatsume et al., "Inhibitory effect of oligoribonucleotide phosphorodithioates against the 3'-exonuclease activity," *Nucleic Acids Symposium Series*, 27:195-196, 1992.
Sallusto et al., "Dendritic cells use macropinocytosis and the mannose receptor to concentrate macromolecules in the major histocompatibility complex class II compartment: downregulation by cytokines and bacterial products," *J Exp Med*, 182(2):389 400, 1995.
Sallusto et al., "Efficient presentation of soluble antigen by cultured human dendritic cells is maintained by granulocyte/macrophage colony-stimulating factor plus interleukin 4 and downregulated by tumor necrosis factor alpha," *Journal of Experimental Medicine*, 179(4)1109-1118, 1994.
Satthaporn et al., "Dendritic cells (II): Role and therapeutic implications in cancer," *J.R. Coll. Surg. Edinb.*, 46(3):159-167, 2001.
Scheel et al., "Immunostimulating capacities of stabilized RNA molecules," *Eur J Immunol*, 34(2)537-547, 2004.
Schirmacher et al., "Intra-pinna anti-tumor vaccination with self-replicating infectious RNA or with DNA encoding a model tumor antigen and a cytokine," *Gene Therapy*, 7(13):1137-1147, 2000.
Schmitt et al., "In vitro induction of a bladder cancer-specific T-cell response by mRNA-transfected dendritic cells," *J Cancer Res Clin Oncol*, 127(3):203-206, 2001.
Schuler, "Murine epidermal Langerhans cells mature into potent immunostimulatory dendritic cells in vitro," *J Exp Med*, 161(3):526-546, 1985.
Schuler-Thurner et al., "Mage-3 and influenza-matrix peptide-specific cytotoxic T cells are inducible in terminal stage HLA-A2.1+ melanoma patients by mature monocyte-derived dendritic cells," *J Immunol*, 165(6):3492-3496, 2000.
Shea et al., "Synthesis, hybridization properties and antivind activity of lipid-oligodeoxynucleotide conjugates," *Nucleic Acids Res*, 18(13):3777-3783, 1990.
Siemens et al., "Vaccines in urologic malignancies, " *Urol. Res.*, 29:152-162, 2001.
Siena et al., "Expansion of Immunostimulatory Dendritic Cells from Peripheral Blood of Patients with Cancer," *The Oncologist*, 2:65-69, 1997.
Sousa, "Use of T7 RNA Polymerase and its Mutants for Incorporation of Nucleoside Analogs into RNA," *Methods in Enzymology*, 317:65-74, 2000.
Steimnan et al., "Dendritic cells: antigen presentation, accessory function and clinical relevance," *Adv Exp Med Biol*, 329:1-9, 1993.

Steinman, "The dendritic cell system and its role in immunogenicity," *Annu Rev Immunol*, 9:271-296, 1991.
Stinchcomb et al., "Isolation and characterisation of a yeast chromosomal replicator," *Nature*, 282(5734): 39-43, 1979.
Strong et al., "Incorporation of β-globin untranslated regions into a Sindbis virus vector for augmentation of heterologous mRNA expression," *Gene Therapy*, 4:624-627, 1997.
Su et al., "Enhanced induction of telomerase-specific CD4(+) T cells using dendritic cells transfected with RNA encoding a chimeric gene product," *Cancer Research*, 62:5041-5048, 2002.
Su et al., "Immunological and Clinical Responses in Metastatic Renal Cancer Patients Vaccinated with Tumor RNA-transfected Dendritic Cells," *Cancer Research*, 63:2127-2133, 2003.
Suda et al., "Hydrodynamic gene delivery: its principles and applications," *Mol. Ther.*, 15(12):2063-2069, 2007.
Sullenger et al., "Emerging clinical applications of RNA," *Nature*, 418(6894):252-258, 2002.
Svinarchuk et al., "Inhibition of HIV proliferation in MT-4 cells by antisense oligonucleotide conjugated to lipophilic groups," *Biochimie*, 75(1-2):49-54, 1993.
Sypniewska et al., "Potential mouse tumor model for pre-clinical testing of mage-specific breast cancer vaccines," *Breast Cancer Research and Treatment*, 74:221-233, 2002.
Tang et al., "Genetic immunization is a simple method for eliciting an immune response," *Nature*, 356(6365):152-154, 1992.
Teufel et al., "Human peripheral blood mononuclear cells transfected with messenger RNA stimulate antigen-specific cytotoxic T-lymphocytes in vitro," *Cell. Mol. Life Sci.*, 62:1755-1762, 2005.
Thurner et al., "Vaccination with mage-3A1 peptide-pulsed mature, monocyte-derived dendritic cells expands specific cytotoxic T cells and induces regression of some metastases in advanced stage IV melanoma," *J Exp Med*, 190(11):1669-1678, 1999.
Tournère et al., "mRNA, degradation machines in eukaryotic cells," *Biochimie.*, 84(8):821-837 2002.
Trinchieri et al., "Cooperation of Toll-like receptor signals in innate immune defence," *Nature Reviews Immunology*, 7:179-190, 2007.
Trojan et al., "Immune reactivity against a novel HLA-A3-restricted influenza virus peptide identified by predicative algorithms and interferon-gamma quantitative PCR," *Journal of Immunotherapy*, 26(1):41-46, 2003.
Tüting et al., "Gene-based strategies for the immunotherapy of cancer," *J Mol Med (Berl.)*, 75:478-491, 1997.
Ueda et al. "Phosphorothioate-containing RNAs show mRNA activity in the prokaryotic translation systems in vitro," *Nucleic Acids Res.*, 19(3):547-552, 1991.
Ulmer et al., "Heterologous protection against influenza by injection of DNA encoding a viral protein," *Science*, 259(5102):1745-1749, 1993.
Ulmer, "An update on the state of the art of DNA vaccines," *Curr Opin Drug Discov Devel*, 4(2):192-197, 2001.
Vassilev et al., "Microparticle-mediated RNA immunization against bovine viral diarrhea virus,", *Vaccine*, 19(15-1 6):2012-2619, 2001.
Verma et al., "Gene therapy—promises, problems and prospects," *Nature*, 389(6648):239-242, 1997.
Verma et al., "Gene therapy: twenty-first century medicine," *Annu. Rev. Biochem.*, 74:711-738, 2005.
Villaret et al., "Identification of genes overexpressed in head and neck squamous cell carcinoma using a combination of complementary DNA subtraction and microarray analysis," *The Laryngoscope*, 110: 374-381, 2000.
Wang et al., "An mRNA stability complex functions with poly(A)-binding protein to stabilize mRNA in vitro," Mol. Cell. Biol., 19(7):4552-4560, 1999.
Wang et al., "Gene inoculation generates immune responses against human immunodeficiency virus type 1," *Proc Natl Acad Sci USA*, 90(9):4156-4160, 1993.
Warren et al., "Uses of granulocyte-macrophage colony-stimulating factor in vaccine development," *Curr Opin Hematol*, 7(3):168-173, 2000.
Watanabe et al., "Induction of wild-type p53 activity in human cancer cells by ribozymes that repair mutant p53 transcripts," *PNAS*, 97(15):8490-8494, 2000.

(56) References Cited

OTHER PUBLICATIONS

Weber et al., "Granulocyte-macrophage-colony-stimulating factor added to a multipeptide vaccine for resected Stage II melanoma," *Cancer*, 97(1):186-200, 2003.

Weide et al., "Results if the First Phase I/II Clinical Vaccination Trial with Direct Infection of mRNA," *J. Immunother.*, 31(2):180-188, 2008.

Weissman et al., "Dendritic cells express and use multiple HIV coreceptors," *Advances in Experimental Medicine and Biology*, 417:401-406, 1997.

Weissman et al., "HIV gag mRNA transfection of dendritic cells (DC) delivers encoded antigen to MHC class I and II molecules, causes DC maturation, and induces a potent human in vitro primary immune response," *J Immunol.*, 165(8):4710-4717, 2000.

Wikipedia Diagram—A Peripheral Blood Mononuclear Cell, Nov. 3, 2011.

Wilusz et al., "Bringing the role of mRNA decay in the control of gene expression into focus," *Trends Genet.* 20(10):491-497, 2004.

Wolff et al., "Direct gene transfer into mouse muscle in vivo," *Science*, 247(4949 Pt. 1):1465-1468, 1990.

Woodberry et al., "Immunogenicity of a human immunodeficiency virus (HIV) polytope vaccine containing multiple HLA A2 HIV CD8(+) cytotoxic T-cells epitopes," *Journal of Virology*, 73(7):5320-5325, 1999.

Wu et al., "Fusion protein vectors to increase protein production and evaluate the immunogenicity of genetic vaccines," *Mol. Ther.*, 2(3):288-297, 2000.

Xu et al., "Identification of differentially expressed genes in human prostate cancer using subtraction and microarray," *Cancer Research*, 60:1677-1682, 2000.

Ying et al., "Cancer therapy using a self-replicating RNA vaccine," *Nat Med*, 5(7):823-827, 1999.

You et al., "A retrogen strategy for presentation of an intracellular tumor antigen as an exogenous antigen by dendritic cells induces potent antitumor T helper and CTL responses," *Cancer Research*, 61:197-205, 2001.

Zhang et al., "Advances in dendritic cell-based vaccine of cancer," *Cancer Biotherapy Radiopharmaceuticals*, 17:601-619, 2002.

Zhou et al., "Papillomavirus capsid protein expression level depends on the match between codon usage and tRNA availability," *Journal of Virology*, 73(6)4972-4982, 1999.

Zhou et al., "RNA melanoma vaccine: induction of antitumor immunity by human glycoprotein 100 mRNA immunization," *Human Gene Therapy*, 10:2719-2724, 1999.

Zitvogel et al. "Therapy of murine tumors with tumor peptide-pulsed dendritic cells: dependence on T cells, B7 costimulation, and T helper cell 1-associated cytokines," *J Exp Med*, 183(1): 87-97, 1996.

Zrihan-Licht et al., "Characterization and molecular cloning of a novel MUC1 protein, devoid of tandem repeats, expressed in human breast cancer tissue," *Eur. J. Biochem.*, 224:787-795, 1994.

\* cited by examiner

Xenopus β-globin 3' untranslated region

▨ GCTTGTTCTTTTTGCAGAAGCTCAGAATAAACGCTCAACTTTGGC

Xenopus β-globin 3' untranslated region

▨ GACTGACTAGGATCTGGTTACCACTAAACCAGCCTCAAGAACACCCGA
ATGGAGTCTCTAAGCTACATAATACCAACTTACACTTACAAAATGTTG
TCCCCAAAATGTAGCCATTCGTATCTGCTCCTAATAAAAGAAAGTT
TCTTCACATTCTA

| Day | -7 | 0 | 14 | 28 | 42 | 56 | 70 | 98 | 126 | 154 | 182 | 210 |
|---|---|---|---|---|---|---|---|---|---|---|---|---|
| Week | -1 | 0 | 2 | 4 | 6 | 8 | 10 | 14 | 18 | 22 | 26 | 30 |
| Inoculation | | | 1 | 2 | 3 | 4 | 5 | 6 | 7 | 8 | 9 | 10 |
| GM-CSF sc | | | x | x | x | x | x | x | x | x | x | x |
| Blood sample | 50 | 40 | 40 | 40 | 40 | 150 | 10 | 10 | 50 | 10 | 10 | 50 |
| Staging | | x | | | | x | | | x | | | x |

FIG. 13

APPLICATION OF MRNA FOR USE AS A THERAPEUTIC AGAINST TUMOUR DISEASES

CROSS-REFERENCE TO RELATED APPLICATIONS

This application is a continuation of U.S. application Ser. No. 14/840,305, filed Aug. 31, 2015, which is a continuation of U.S. application Ser. No. 14/325,850, filed Jul. 8, 2014, now U.S. Pat. No. 9,155,788, which is a divisional of U.S. application Ser. No. 13/106,548, filed May 12, 2011, now abandoned, which is a divisional of U.S. application Ser. No. 10/870,110, filed Jun. 18, 2004, now U.S. Pat. No. 8,217,016, which is a continuation under 35 U.S.C. §111(a) of International Application No. PCT/EP02/14577, filed Dec. 19, 2002, which claims priority under 35 U.S.C. §119 to German Patent Application No.: 101 62 480.8, filed Dec. 19, 2001. The entire text of each of the above-referenced disclosures is specifically incorporated herein by reference without disclaimer.

REFERENCE TO SEQUENCE LISTING

This application contains a Sequence Listing which has been submitted in text format via EFS-Web and is hereby incorporated by reference in its entirety. Said text file, created Dec. 9, 2015, is named CRVCP0009USC6.txt and is ~2 KB in size.

BACKGROUND OF THE INVENTION

The present invention relates to a pharmaceutical composition comprising at least one mRNA comprising at least one coding region for at least one antigen from a tumour, in combination with an aqueous solvent and preferably a cytokine, e.g. GM-CSF, and a process for the preparation of the pharmaceutical composition. The pharmaceutical composition according to the invention is used in particular for therapy and/or prophylaxis against cancer.

Gene therapy and genetic vaccination are molecular medicine methods which, when used in the therapy and prevention of diseases, will have considerable effects on medical practice. Both methods are based on the introduction of nucleic acids into cells or into tissues of the patient and on subsequent processing of the information coded by the nucleic acids introduced, i.e. expression of the desired polypeptides.

The conventional procedure of methods of gene therapy and of genetic vaccination to date is the use of DNA to insert the required genetic information into the cell. Various methods for introducing DNA into cells have been developed in this connection, such as e.g. calcium phosphate transfection, polyprene transfection, protoplast fusion, electroporation, microinjection and lipofection, whereas lipofection in particular having emerged as a suitable method.

A further method which has been proposed in particular in the case of genetic vaccination methods is the use of DNA viruses as DNA vehicles. Such viruses have the advantage that because of their infectious properties a very high transfection rate can be achieved. The viruses used are genetically modified, so that no functional infectious particles are formed in the transfected cell. In spite of this safety precaution, however, a certain risk of uncontrolled propagation of the genes having a gene therapy action and the viral genes introduced cannot be ruled out because of possible recombination events.

The DNA introduced into the cell is conventionally integrated into the genome of the transfected cell to a certain extent. On the one hand this phenomenon can exert a desired effect, since a long-lasting action of the DNA introduced can thereby be achieved. On the other hand, the integration into the genome results in a substantial risk of gene therapy. Thus e.g. the DNA introduced may be inserted into an intact gene, which represents a mutation which interferes or even completely switches off the function of the endogenous gene. On the one hand enzyme systems which are essential for the cell may be switched off by such integration events, and on the other hand there is also the danger of a transformation of the cell modified in this way into a degenerated state if a gene which is decisive for regulation of cell growth is modified by the integration of the foreign DNA. A risk of the development of cancer therefore cannot be ruled out when using DNA viruses as gene therapeutics and vaccines. In this connection it is also to be noted that for effective expression of the genes introduced into the cell, the corresponding DNA vehicles contain a strong promoter, e.g. the viral CMV promoter. Integration of such promoters into the genome of the treated cell can lead to undesirable changes in the regulation of gene expression in the cell.

A further disadvantage of the use of DNA as gene therapeutics and vaccines is the induction of pathogenic anti-DNA antibodies in the patient, causing a possibly fatal immune response.

In contrast to DNA, the use of RNA as a gene therapeutic or vaccine is to be classified as substantially safer. In particular, RNA does not involve the risk of being integrated into the genome of the transfected cell in a stable manner. Furthermore, no viral sequences, such as promoters, are necessary for effective transcription. Moreover, RNA is degraded considerably more easily in vivo. Apparently because of the relatively short half-life of RNA in the blood circulation compared with DNA, no anti-RNA antibodies have been detected to date. RNA can therefore be regarded as the molecule of choice for molecular medicine therapy methods.

Nevertheless, medical methods based on RNA expression systems still require a solution to some fundamental problems before they are used more widely. One of the problems of using RNA is reliable cell- or tissue-specific efficient transfer of the nucleic acid. Since RNA usually proves to be very unstable in solution, it has not hitherto been possible, or has been possible only in a very inefficient manner, to use RNA as a therapeutic or vaccine by the conventional methods which are used with DNA.

RNA-degrading enzymes, so-called RNAases (ribonucleases), are responsible for the instability. Even the smallest impurities of ribonucleases are sufficient to degrade RNA in solution completely. The natural degradation of mRNA in the cytoplasm of cells is very finely regulated. Several mechanisms are known in this respect. Thus, the terminal structure is of decisive importance for a functional mRNA. At the 5'-end is the so-called "cap structure" (a modified guanosine nucleotide), and at the 3'-end a sequence of up to 200 adenosine nucleotides (the so-called poly-A tail). The RNA is recognized as mRNA and the degradation is regulated via these structures. Moreover, there are further processes which stabilize or destabilize RNA. Many of these processes are still unknown, but an interaction between the RNA and proteins often appears to be decisive for this. For example, an "mRNA surveillance system" has recently been described (Hellerin and Parker, Annu. Rev. Genet. 1999, 33: 229 to 260), in which incomplete or nonsense mRNA is recognized by certain feedback protein interactions in the cytosol and is rendered accessible to degradation, the majority of these processes being performed by exonucleases.

Some measures for increasing the stability of RNA and thereby rendering possible its use as a gene therapeutic or RNA vaccine have been proposed in the prior art.

To solve the abovementioned problems of the instability of RNA ex vivo, EP-A-1083232 proposes a process for introduction of RNA, in particular mRNA, into cells and organisms, in which the RNA is in the form of a complex with a cationic peptide or protein.

WO 99/14346 describes further processes for stabilizing mRNA. In particular, modifications of the mRNA which stabilize the mRNA species against the degradation by RNases are proposed. Such modifications concern on the one hand stabilization by sequence modifications, in particular reduction of the C and/or U content by base elimination or base substitution. On the other hand, chemical modifications, in particular the use of nucleotide analogues, and 5'- and 3'-blocking groups, an increased length of the poly-A tail and complexing of the mRNA with stabilizing agents and combinations of the measures mentioned, are proposed.

The U.S. Pat. No. 5,580,859 and U.S. Pat. No. 6,214,804 disclose, inter alia, mRNA vaccines and therapeutics in the context of "transient gene therapy" (TGT). Various measures for increasing the translation efficiency and the mRNA stability based above all on untranslated sequence regions are described.

Bieler and Wagner (in: Schleef (ed.), Plasmids for Therapy and Vaccination, chapter 9, pages 147 to 168, Wiley-VCH, Weinheim, 2001) report on the use of synthetic genes in connection with gene therapy methods using DNA vaccines and lentiviral vectors. The construction of a synthetic gag gene derived from HIV-1, in which the codons were modified (alternative codon usage) compared with the wild-type sequence such that they corresponded to the use of codons which are to be found in highly expressed mammalian genes, is described. By this means, the A/T content in particular was reduced compared with the wild-type sequence. The authors find in particular an increased expression rate of the synthetic gag gene in transfected cells. Furthermore, in mice an increased formation of antibodies against the gag protein was observed in mice immunized with the synthetic DNA construct, and also an increased cytokine release in vitro in transfected spleen cells of mice. Finally, an induction of a cytotoxic immune response was to be found in mice immunized with the gag expression plasmid. The authors of this article attribute the improved properties of their DNA vaccine substantially to a change, caused by the optimized codon usage, to the nucleo-cytoplasmic transporation of the mRNA expressed by the DNA vaccine. In contrast, the authors consider the effect of the modified codon usage on the translation efficiency to be low.

DETAILED DESCRIPTION OF THE INVENTION

The present invention is therefore based on the object of providing a new system for gene therapy and genetic vaccination for tumours which overcomes the disadvantages associated with the properties of DNA therapeutics and vaccines.

This object is solved by the embodiments of the present invention characterized in the claims.

In particular, a pharmaceutical composition comprising at least one mRNA comprising at least one coding region for at least one antigen from a tumour, in combination with an aqueous solvent, is provided.

According to the invention, the expression "antigen from a tumour" means that the corresponding antigen is expressed in cells associated with a tumour. According to the invention, antigens from tumours are therefore in particular those which are produced in the degenerated cells themselves. These are preferably antigens located on the surface of the cells. Furthermore, however, antigens from tumours are also those which are expressed in cells which are (were) not themselves (or originally themselves) degenerated but are associated with the tumour in question. These also include e.g. antigens which are connected with tumour-supplying vessels or (re)formation thereof, in particular those antigens which are associated with neovascularization or angiogenesis, e.g. growth factors, such as VEGF, bFGF etc. Such antigens connected with a tumour furthermore also include those from cells of the tissue embedding the tumour. Corresponding antigens of connective tissue cells, e.g. antigens of the extracellular matrix, are to be mentioned here.

According to the invention, in the pharmaceutical composition one (or more) mRNAs is used for therapy or inoculation, i.e. vaccination, for treatment or prevention (prophylaxis) of cancer diseases. The vaccination is based on the introduction of an antigen (or several antigens) of a tumour, in the present case the genetic information for the antigen in the form of the mRNA which codes for the antigen(s), into the organism, in particular into the cell. The mRNA contained in the pharmaceutical composition is translated into the (tumour) antigen, i.e. the polypeptide or antigenic peptide coded by the modified mRNA is expressed, as a result of which an immune response directed against this polypeptide or antigenic polypeptide is stimulated. In the present case of the use as genetic vaccines for treatment of cancer, the immune response is therefore achieved by introduction of the genetic information for antigens from a tumour, in particular proteins which are expressed exclusively on cancer cells, in that a pharmaceutical composition according to the invention which comprises an mRNA which codes for such a cancer antigen is administered. By this means, the cancer antigen(s) is (are) expressed in the organism, as a result of which an immune response which is directed effectively against the cancer cells is provoked.

In its use as a vaccine, the pharmaceutical composition according to the invention is to be considered in particular for treatment of cancer diseases (the mRNA preferably coding for a tumour-specific surface antigen (TSSA), e.g. for treatment of malignant melanoma, colon carcinoma, lymphomas, sarcomas, small-cell pulmonary carcinoma, blastomas etc. Specific examples of tumour antigens are, inter alia, 707-AP, AFP, ART-4, BAGE, β-catenine/m, Bcr-abl, CAMEL, CAP-1, CASP-8, CDC27/m, CDK4/m, CEA, CT, Cyp-B, DAM, ELF2M, ETV6-AML1, G250, GAGE, GnT-V, Gp100, HAGE, HER-2/neu, HLA-A*0201-R170I, HPV-E7, HSP70-2M, HAST-2, hTERT (or hTRT), iCE, KIAA0205, LAGE, LDLR/FUT, MAGE, MART-1/melan-A, MC1R, myosine/m, MUC1, MUM-1, -2, -3, NA88-A, NY-ESO-1, p190 minor bcr-abl, Pml/RARα, PRAME, PSA, PSM, RAGE, RU1 or RU2, SAGE, SART-1 or SART-3, TEL/AML1, TPI/m, TRP-1, TRP-2, TRP-2/INT2 and WT1.

According to a further preferred embodiment, the antigen(s) from a tumour is or are a polyepitope of the antigen(s) from a tumour. A "polyepitope" of an antigen or several antigens is an amino acid sequence in which several or many regions of the antigen(s) which interact with the antigen-binding part of an antibody or with a T cell receptor are represented. In this context, the polyepitope can be complete and non-modified. However, according to the present invention it can also be modified, in particular to optimize the antibody/antigen and T cell receptor/antigen interaction, respectively. A modification compared with the wild-type polyepitope can include e.g. a deletion, addition and/or substitution of one or more amino acid residues. Accordingly, in the mRNA of the present invention which codes for the modified polyepitope, one or more nucleotides is/are removed, added and/or replaced, compared with the mRNA which codes for the wild-type polyepitope.

In order to increase the stability of the (m)RNA contained in the pharmaceutical composition of the present invention, each (m)RNA contained in the pharmaceutical composition preferably has one or more modifications, in particular chemical modifications, which contribute towards increasing the half-life of the (m)RNA (one or more) in the organism or improve the transfer of the (m)RNA (one or more) into the cell.

For example, in the sequences of eukaryotic mRNAs, there are destabilizing sequence elements (DSE) to which signal proteins bind and regulate the enzymatic degradation of the mRNA in vivo. For further stabilization of the modified mRNA preferably contained in the pharmaceutical composition according to the invention, where appropriate in the region which codes for at least one antigen from a tumour one or more modifications compared with the corresponding region of the wild-type mRNA are carried out, so that no destabilizing sequence elements are present. According to the invention, it is of course also preferable, where appropriate, to eliminate from the mRNA DSEs present in the untranslated regions (3'- and/or 5'-UTR).

Such destabilizing sequences are e.g. AU-rich sequences ("AURES"), which occur in 3'-UTR sections of numerous unstable mRNAs (Caput et al., Proc. Natl. Acad. Sci. USA 1986, 83: 1670 to 1674). The RNA molecules contained in the pharmaceutical composition according to the invention are therefore preferably modified compared with the wild-type mRNA such that they contain no such destabilizing sequences. This also applies to those sequence motifs which are recognized by possible endonucleases, e.g. the sequence GAACAAG, which is contained in the 3'-UTR segment of the gene which codes for the transferrin receptor (Binder et al., EMBO J. 1994, 13: 1969 to 1980). These sequence motifs are also preferably eliminated in the modified mRNA of the pharmaceutical composition according to the invention.

A skilled person in the art is familiar with various processes which are suitable for substitution of codons in the modified mRNA according to the invention. In the case of relatively short coding regions (which code for biologically active or antigenic peptides) e.g. the total mRNA can be synthesized chemically using standard techniques.

Nevertheless, base substitutions are preferably introduced, using a DNA matrix for the preparation of the modified mRNA with the aid of techniques of the usual targeted mutagenesis; Maniatis et al., Molecular Cloning: A Laboratory Manual, Cold Spring Harbor Laboratory Press, 3rd ed., Cold Spring Harbor, N. Y., 2001.

In this process, for the preparation of the mRNA, a corresponding DNA molecule is therefore transcribed in vitro. This DNA matrix has a suitable promoter, e.g. a T7 or SP6 promoter, for the in vitro transcription, which is followed by the desired nucleotide sequence for the mRNA to be prepared and a termination signal for the in vitro transcription. According to the invention, the DNA molecule which forms the matrix of the RNA construct to be prepared is prepared by fermentative proliferation and subsequent isolation as part of a plasmid which can be replicated in bacteria. Plasmids which may be mentioned as suitable for the present invention are e.g. the plasmids pT7TS (GenBank Access Number U26404; Lai et al., Development 1995, 121: 2349 to 2360; cf. also FIG. 8), pGEM® serie, e.g. pGEM®-1 (GenBank Access Number X65300; from Promega) and pSP64 (GenBank Access Number X65327); cf. also Mezei and Storts, Purification of PCR Products, in: Griffin and Griffin (ed.), PCR Technology: Current Innovation, CRC Press, Boca Raton, Fla., 2001.

Using short synthetic DNA oligonucleotides which contain short single-stranded transitions at the cleavage sites formed or genes prepared by chemical synthesis, the desired nucleotide sequence can thus be cloned into a suitable plasmid by molecular biology methods with which a skilled person in the art is familiar (cf. Maniatis et al., see above). The DNA molecule is then excised the plasmid, in which it can be present in one or multiple copy, by digestion with restriction endonucleases.

The modified mRNA contained in the pharmaceutical composition according to the invention can moreover have a 5'-cap structure (a modified guanosine nucleotide). Examples of cap structures which may be mentioned are m7G(5')ppp (5'(A,G(5')ppp(5')A and G(5')ppp(5')G.

According to a further preferred embodiment of the present invention, the modified mRNA contains a poly($A^+$) tail of at least about 25, in particular at least about 30, preferably at least about 50 nucleotides, more preferably at least about 70 nucleotides, particularly preferably at least about 100 nucleotides. However, the poly($A^+$) tail can also comprise 200 and more nucleotides.

For efficient translation of the mRNA, effective binding of the ribosomes to the ribosome binding site (Kozak sequence: GCCGCCACCAUGG (SEQ ID NO: 2), AUG forms the start codon) is necessary. In this respect, it has been found that an increased A/U content around this site renders possible a more efficient ribosome binding to the mRNA.

It is furthermore possible to insert one or more so-called IRES ("internal ribosomal entry site) into the mRNA. An IRES can thus function as the single ribosome binding site, but it can also serve to provide an mRNA which codes several peptides or polypeptides which are to be translated by the ribosomes independently of one another ("multicistronic" or "polycistronic" mRNA). Examples of IRES sequences which can be used according to the invention are those from picornaviruses (e.g. FMDV), pestviruses (CFFV), polioviruses (PV), encephalomyocarditis viruses (ECMV), foot and mouth disease viruses (FMDV), hepatitis C viruses (HCV), classical swine fever viruses (CSFV), mouse leukoma virus (MLV), simian immunodeficiency viruses (SIV) or cricket paralysis viruses (CrPV).

According to a further preferred embodiment of the present invention, the mRNA has, in the 5'- and/or 3'-untranslated regions, stabilizing sequences which are capable of increasing the half-life of the mRNA in the cytosol.

These stabilizing sequences can have a 100% sequence homology to naturally occurring sequences which occur in viruses, bacteria and eukaryotes, but can also be partly or completely of synthetic nature. Examples of stabilizing sequences which can be used in the present invention and which may be mentioned are the untranslated sequences (UTR) of the β-globin gene, e.g. from *Homo sapiens* or *Xenopus laevis*. Another example of a stabilizing sequence has the general formula (C/U)CCAN$_x$CCC(U/A)Py$_x$UC(C/U)CC (SEQ ID NO: 1), which is contained in the 3'-UTR of the very stable mRNA which codes for α-globin, α-(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a skilled person in the art.

For further stabilization of the mRNA, it is moreover preferred to contain at least one analogue of naturally occurring nucleotides. This is based on the fact that the RNA-degrading enzymes occurring in the cells preferentially recognize naturally occurring nucleotides as a substrate. The degradation of RNA can therefore be made difficult by insertion of nucleotide analogues, whereby the effect on the translation efficiency on insertion of these analogues, in particular in the coding region of the mRNA, can have a positive or negative effect on the translation efficiency.

In a list which is in no way conclusive, examples which may be mentioned of nucleotide analogues which can be used according to the invention are phosphoroamidates, phosphorothioates, peptide nucleotides, methylphosphonates, 7-deazaguanosine, 5-methylcytosine and inosine. The preparation of such analogues is known to a skilled person in the art e.g. from the U.S. Pat. No. 4,373,071, U.S. Pat. No. 4,401,796, U.S. Pat. No. 4,415,732, U.S. Pat. No. 4,458,066, U.S. Pat. No. 4,500,707, U.S. Pat. No. 4,668,777, U.S. Pat. No. 4,973,679, U.S. Pat. No. 5,047,524, U.S. Pat. No. 5,132,418, U.S. Pat. No. 5,153,319, U.S. Pat. Nos. 5,262,530 and 5,700,642. According to the invention, such analogues can occur in untranslated and translated regions of the modified mRNA.

Furthermore, effective transfer of the preferably modified mRNA into the cells to be treated or the organism to be treated can be improved if the mRNA is associated with a cationic or polycationic agent, in particular a corresponding peptide or protein, or bound thereto. The mRNA is therefore present in the pharmaceutical composition according to the invention preferably in a form complexed or condensed with such an agent. In particular, the use of protamine as a polycationic, nucleic acid-binding protein is particularly effective in this context. The use of other cationic peptides or proteins, such as poly-L-lysine, poly-L-arginine or histones, is furthermore also possible. This procedure for stabilizing the modified mRNA is described in EP-A-1083232, the disclosure content of which in this respect is included in its full scope in the present invention.

The mRNA modified according to the invention can moreover also contain, in addition to the peptide or polypeptide which is antigenic or active in gene therapy, at least one further functional section which e.g. codes for a cytokine which promotes the immune response, (monokine, lymphokine, interleukin or chemokine, such as IL-1, IL-2, IL-3, IL-4, IL-5, IL-6, IL-7, IL-8, IL-9, IL-10, IL-12, IFN-α, IFN-γ, GM-CFS, LT-α or growth factors, such as hGH).

The pharmaceutical composition according to the invention can further comprise one or more adjuvants to increase the immunogenicity. "Adjuvant" here is to be understood as meaning any chemical or biological compound which promotes a specific immune response. Various mechanisms are possible in this respect, depending on the various types of adjuvants used. For example, compounds which promote endocytosis of the modified mRNA contained in the pharmaceutical composition by dendritic cells (DC) form a first class of adjuvants which can be used. Other compounds which allow the maturation of the DC, e.g. lipopolysaccharides, TNF-α or CD40 ligand, are a further class of suitable adjuvants. Generally, any agent which influences the immune system of the nature of a "warning signal" (LPS, GP96, oligonucleotides with the CpG motif) or cytokines, in particular GM-CSF, can be used as an adjuvant which allow an immune response against an antigen which is coded by the modified mRNA to be increased and/or influenced in a targeted manner. In particular, the abovementioned cytokines are preferred in this context. Further known adjuvants are aluminium hydroxide, Freund's adjuvant and the abovementioned stabilizing cationic peptides or polypeptides, such as protamine. Lipopeptides, such as Pam3Cys, are also particularly suitable for use as adjuvants in the pharmaceutical composition of the present invention; c.f. Deres et al., Nature 1989, 342: 561-564.

Further particularly suitable adjuvants are moreover (other) RNA or also mRNA species, which can be added to the pharmaceutical composition of the present invention to increase the immunogenicity. Such adjuvant RNA is advantageously chemically modified for stabilization ("cis modification" or "cis stabilization"), for example by the abovementioned nucleotide analogues, in particular phosphorothioate-modified nucleotides, or by the above further measures for stabilization of RNA. A further advantageous possibility of stabilization is complexing or association ("trans association" or "trans modification" and "trans stabilization", respectively) with the abovementioned cationic or polycationic agents, e.g. with protamine.

According to a further advantageous embodiment, the stability of the RNA molecules contained in the pharmaceutical composition (mRNA, coding for a tumour antigen, and optionally adjuvant (m)RNA) is increased by one or more RNase inhibitors. Preferred RNase inhibitors are peptides or proteins, in particular those from the placenta (e.g. from the human placenta) or pancreas. Such RNase inhibitors can also be in a recombinant form. A specific example of an RNase inhibitor is RNasin®, which is commercially obtainable, e.g. from Promega. Such RNase inhibitors can be used generally for stabilizing RNA. A pharmaceutical composition comprising at least one RNA, in particular mRNA, which codes for at least one antigen, and at least one RNase inhibitor as defined above, optionally in combination with a pharmaceutically acceptable solvent, carrier and/or vehicle, is therefore also provided generally according to the invention. Corresponding antigens in a general form and solvents, carriers and vehicles are defined below. In respect of preferred tumour antigens, reference is made to the statements in this respect concerning the preferred pharmaceutical composition comprising at least one mRNA which codes for at least one antigen from a tumour.

The pharmaceutical composition according to the invention preferably comprises, in addition to the aqueous solvent and the mRNA, one or more further pharmaceutically acceptable carrier(s) and/or one or more further pharmaceutically acceptable vehicle(s). Corresponding routes for suitable formulation and preparation of the pharmaceutical composition according to the invention are disclosed in "Remington's Pharmaceutical Sciences" (Mack Pub. Co., Easton, Pa., 1980), which is a constituent in its full content of the disclosure of the present invention. Possible carrier substances for parenteral administration are e.g., in addition to sterile water or sterile saline solutions as aqueous solvents, also polyalkylene glycols, hydrogenated naphthalene and, in particular, biocompatible lactide polymers, lactide/glycolide copolymers or polyoxyethylene/polyoxypropylene copolymers. Compositions according to the invention can comprise filler substances or substances such as lactose, mannitol, substances for covalent linking of polymers, such as e.g. polyethylene glycol, to inhibitors according to the invention, complexing with metal ions or inclusion of materials in or on particular preparations of a polymer compound, such as e.g. polylactate, polyglycolic acid or hydrogel, or on liposomes, microemulsions, micelles, unilamellar or multilamellar vesicles, erythrocyte fragments or spheroplasts. The particular embodiments of the compositions are chosen according to the physical properties, for example in respect of solubility, stability, bioavailability or degradability. Controlled or constant release of the active compound component according to the invention in the composition includes formulations based on lipophilic depots (e.g. fatty acids, waxes or oils).

Coatings of substances according to the invention or compositions comprising such substances, that is to say coatings with polymers (e.g. polyoxamers or polyoxamines) are also disclosed in the context of the present invention. Substances or compositions according to the invention can furthermore have protective coatings, e.g. protease inhibitors or permeability-increasing agents. Preferred aqueous carrier materials are e.g. water for injection (WFI) or water buffered with phosphate, citrate or acetate etc., whereby the pH typically being adjusted to 5.0 to 8.0, preferably 6.0 to 7.0. The aqueous solvent or the further carrier(s) or the further vehicle(s) will additionally preferably comprise salt constituents, e.g. sodium chloride, potassium chloride or other components which render the solution e.g. isotonic. Aqueous solvents or the further carrier(s) or the further vehicle(s) can furthermore comprise, in addition to the abovementioned constituents, additional components, such as human serum albumin (HSA), Polysorbate 80, sugars or amino acids.

The method and mode of administration and the dosage of the pharmaceutical composition according to the invention depend on the disease to be treated and the stage of advancement thereof, and also the body weight, the age and the sex of the patient.

The concentration of the modified mRNA in such formulations can therefore vary within a wide range from 1 µg to 100 mg/ml. The pharmaceutical composition according to the invention is preferably administered to the patient parenterally, e.g. intravenously, intraarterially, subcutaneously or intramuscularly. It is also possible to administer the pharmaceutical composition topically or orally. The pharmaceutical composition according to the invention is preferably administered intradermally. A transdermal administration with the aid of electric currents or by osmotic forces is furthermore possible. The pharmaceutical composition of the present invention can moreover be injected locally into a tumour.

Thus, a method for treatment or a vaccination method for prevention of cancer diseases or the abovementioned diseases which comprises administration of the pharmaceutical composition according to the invention to a patient, in particular a human, is thus also provided according to the invention.

According to a preferred embodiment of the treatment or vaccination method or in the use, defined above, of the mRNA according to the invention which codes for at least one antigen from a tumour for the preparation of a pharmaceutical composition for treatment and/or prevention of cancer diseases one or more cytokine(s) is administered to the patient, in addition to the pharmaceutical composition according to the invention.

A treatment or vaccination method comprising administration of at least one RNA, preferably mRNA, which code(s) for at least one antigen from a tumour (in accordance with the above definition) and is (are) optionally stabilized in accordance with the above statements, and at least one cytokine, e.g. one or more of the abovementioned cytokines, in particular GM-CSF, to a patient, in particular a human, is therefore also provided generally according to the invention. The method is used in particular for treatment and/or prevention of corresponding cancer diseases (e.g. the above cancer diseases). The present invention is accordingly also directed generally to a pharmaceutical composition comprising at least one RNA, preferably mRNA, which code(s) for at least one antigen from a tumour (according to the above definition) and is (are) optionally stabilized in accordance with the above statements, and at least one cytokine, e.g. one or more of the abovementioned cytokines, such as GM-CSF, preferably in combination with a pharmaceutically acceptable carrier and/or vehicle, e.g. an aqueous solvent, or one or more of the carriers, solvents or vehicles defined above. The use of cytokines, e.g. one or more of the abovementioned cytokines, in particular GM-CSF, in combination with one or more RNA molecule(s) as defined above, for treatment and/or prevention of cancer diseases (e.g. cancer diseases listed above) is thus also disclosed according to the invention.

According to a further preferred embodiment of the present invention, the cytokine, e.g. GM-CSF, is administered simultaneously with or, which is more preferable, before or after the pharmaceutical composition comprising the mRNA which codes for at least one antigen from a tumour (or is used for the preparation of a corresponding medicament for simultaneous administration with or for administration before or after the abovementioned (m)RNA). The administration of the cytokine, in particular GM-CSF, is very particularly preferably carried out shortly before (e.g. about 15 min or less, e.g. about 10 or about 5 min) or a relatively short time (e.g. about 5, 10, 15, 30, 45 or 60 min) after or a longer time (e.g. about 2, 6, 12, 24 or 36 h) after the administration of the pharmaceutical composition defined above or generally after the (m)RNA of at least one which codes for at least one antigen from a tumour.

The application of the cytokine, e.g. GM-CSF, can be carried out in this context by the same route as the pharmaceutical composition according to the invention or the at least one (m)RNA which codes for at least one antigen from a tumour or in a manner separate from this. Suitable administration routes and also the suitable formulation possibilities in respect of the cytokine(s) can be found from the above statements in respect of the pharmaceutical compositions according to the invention. In the case of a human patient, a GM-CSF dose of 100 micrograms/m$^2$ in particular is advisable. The administration of the cytokine, e.g. GM-CSF, is particularly preferably carried out by an s.c. injection.

The pharmaceutical compositions of the present invention or the RNA which codes for an antigen from a tumour and where appropriate, in association therewith, the cytokine(s) are preferably administered in the form of interval doses. For example, a dose of a pharmaceutical composition according to the invention can be administered in relatively short intervals, e.g. daily, every second day, every third day etc., or, which is more preferable, in longer intervals, e.g. once weekly, once in two weeks, once in three weeks, once a month etc. The intervals can also be changeable in this context, whereby it being necessary in particular to take into account the immunological parameters of the patient. For example, the administration of a pharmaceutical composition according to the invention (and where appropriate, in association therewith, also the administration of the cytokine(s)) can follow a treatment plan in which the interval is shorter, e.g. once in two weeks, at the start of the treatment and then, depending on the course of treatment or the appropriately determined immunological parameters of the patient, the interval is lengthened to e.g. once a month. A therapy plan tailor-made to the particular individual can thus be applied according to the patient, in particular his condition and his immunological parameters.

The present invention also provides a process for the preparation of the pharmaceutical composition defined above, comprising the steps:
(a) preparation of a cDNA library, or a part thereof, from tumour tissue of a patient,
(b) preparation of a matrix for in vitro transcription of RNA with the aid of the cDNA library or a part thereof and
(c) in vitro transcribing of the matrix.

The tumour tissue of the patient can be obtained e.g. by a simple biopsy. However, it can also be provided by surgical removal of tumour-invaded tissue. The preparation of the cDNA library or a part thereof according to step (a) of the preparation process of the present invention can moreover be carried out after the corresponding tissue has been deep-frozen for storage, preferably at temperatures below −70° C. For preparation of the cDNA library or a part thereof, isolation of the total RNA, e.g. from a tumour tissue biopsy, is first carried out. Processes for this are described e.g. in Maniatis et al., supra. Corresponding kits are furthermore commercially obtainable for this, e.g. from Roche AG (e.g. the product "High Pure RNA Isolation Kit"). The corresponding poly($A^+$) RNA is isolated from the total RNA in accordance with processes known to a person skilled in the art (cf. e.g. Maniatis et al., supra). Appropriate kits are also commercially obtainable for this. An example is the "High Pure RNA Tissue Kit" from Roche AG. Starting from the poly($A^+$) RNA obtained in this way, the cDNA library is then prepared (in this context cf. also e.g. Maniatis et al., supra). For this step in the preparation of the cDNA library also, commercially obtainable kits are available to a person skilled in the art, e.g. the "SMART PCR cDNA Synthesis Kit" from Clontech Inc. The individual sub-steps from the poly($A^+$) RNA to the double-stranded cDNA is shown schematically in FIG. 11 by the example of the process in accordance with the "SMART PCR cDNA Synthesis Kit" from Clontech Inc.

According to step (b) of the above preparation process, starting from the cDNA library (or a part thereof), a matrix is synthesized for the in vitro transcription. According to the invention, this is effected in particular by cloning the cDNA fragments obtained into a suitable RNA production vector. The suitable DNA matrix and the plasmids which are preferred according to the invention are already mentioned above in connection with the preparation of the mRNA for the pharmaceutical composition according to the invention.

For in vitro transcription of the matrix prepared in step (b) according to the invention, these are first linearized with a corresponding restriction enzyme, if they are present as circular plasmid (c)DNA. Preferably, the construct cleaved in this way is purified once more, e.g. by appropriate phenol/chloroform and/or chloroform/phenol/isoamyl alcohol mixtures, before the actual in vitro transcription. By this means it is ensured in particular that the DNA matrix is in a protein-free form. The enzymatic synthesis of the RNA is then carried out starting from the purified matrix. This sub-step takes place in an appropriate reaction mixture comprising the linearized, protein-free DNA matrix in a suitable buffer, to which a ribonuclease inhibitor is preferably added, using a mixture of the required ribonucleotide triphosphates (rATP, rCTP, rUTP and rGTP) and a sufficient amount of a RNA polymerase, e.g. T7 polymerase. The reaction mixture is present here in RNase-free water. Preferably, a CAP analogue is also added during the actual enzymatic synthesis of the RNA. After an incubation of an appropriately long period, e.g. 2 h, at 37° C., the DNA matrix is degraded by addition of RNase-free DNase, incubation preferably being carried out again at 37° C.

Preferably, the RNA prepared in this way is precipitated by means of ammonium acetate/ethanol and, where appropriate, washed once or several times with RNase-free ethanol. Finally, the RNA purified in this way is dried and, according to a preferred embodiment, is taken up in RNase-free water. The RNA prepared in this way can moreover be subjected to several extractions with phenol/chloroform or phenol/chloroform/isoamyl alcohol.

According to a further preferred embodiment of the preparation process defined above, only a part of a total cDNA library is obtained and converted into corresponding mRNA molecules. According to the invention, a so-called subtraction library can therefore also be used as part of the total cDNA library in order to provide the mRNA molecules according to the invention. A preferred part of the cDNA library of the tumour tissue codes for the tumour-specific antigens. For certain tumours, the corresponding antigens are known. According to a further preferred embodiment, the part of the cDNA library which codes for the tumour-specific antigens can first be defined (i.e. before step (a) of the process defined above). This is preferably effected by determining the sequences of the tumour-specific antigens by an alignment with a corresponding cDNA library from healthy tissue.

The alignment according to the invention comprises in particular a comparison of the expression pattern of the healthy tissue with that of the tumour tissue in question. Corresponding expression patterns can be determined at the nucleic acid level e.g. with the aid of suitable hybridization experiments. For this e.g. the corresponding (m)RNA or cDNA libraries of the tissue can in each case be separated in suitable agarose or polyacrylamide gels, transferred to membranes and hybridized with corresponding nucleic acid probes, preferably oligonucleotide probes, which represent the particular genes (northern and southern blots, respectively). A comparison of the corresponding hybridizations thus provides those genes which are expressed either exclusively by the tumour tissue or to a greater extent therein.

According to a further preferred embodiment, the hybridization experiments mentioned are carried out with the aid of a diagnosis by microarrays (one or more microarrays). A corresponding DNA microarray comprises a defined arrangement, in particular in a small or very small space, of nucleic acid, in particular oligonucleotide, probes, each probe representing e.g. in each case a gene, the presence or absence of which is to be investigated in the corresponding (m)RNA or cDNA library. In an appropriate microarrangement, hundreds, thousands and even tens to hundreds of thousands of genes can be represented in this way. For analysis of the expression pattern of the particular tissue, either the poly($A^+$) RNA or, which is preferable, the corresponding cDNA is then marked with a suitable marker, in particular fluorescence markers are used for this purpose, and brought into contact with the microarray under suitable hybridization conditions. If a cDNA species binds to a probe molecule present on the microarray, in particular an oligonucleotide probe molecule, a more or less pronounced fluorescence signal, which can be measured with a suitable detection apparatus, e.g. an appropriately designed fluorescence spectrometer, is accordingly observed. The more the cDNA (or RNA) species is represented in the library, the greater will be the signal, e.g. the fluorescence signal. The corresponding microarray hybridization experiment (or several or many of these) is (are) carried out separately for the tumour tissue and the healthy tissue. The genes expressed exclusively or to an increased extent by the tumour tissue can therefore be concluded from the difference between the signals read from the microarray experiments. Such DNA microarray analyses are described e.g. in Schena (2002), Microarray Analysis, ISBN 0-471-41443-3, John Wiley & Sons, Inc., New York, the disclosure content in this respect of this document being included in its full scope in the present invention.

However, the establishing of tumour tissue-specific expression patterns is in no way limited to analyses at the nucleic acid level. Methods known from the prior art which serve for expression analysis at the protein level are of course also familiar to a person skilled in the art. There may be mentioned here in particular techniques of 2D gel electrophoresis and mass spectrometry, whereby these techniques advantageously also can be combined with protein biochips (i.e., microarrays at the protein level, in which e.g. a protein extract from healthy or tumour tissue is brought into contact with antibodies and/or peptides applied to the microarray substrate). With regard to the mass spectroscopy methods, MALDI-TOF ("matrix assisted laser desorption/ionization-time of flight") methods are to be mentioned in this respect. The techniques mentioned for protein chemistry analysis to obtain the expression pattern of tumour tissue in comparison with healthy tissue are described e.g. in Rehm (2000) Der Experimentator: Proteinbiochemie/Proteomics [The Experimenter: Protein Biochemistry/Proteomics], Spektrum Akademischer Verlag, Heidelberg, 3rd ed., to the disclosure content of which in this respect reference is expressly made expressis verbis in the present invention. With regard to protein microarrays, reference is moreover again made to the statements in this respect in Schena (2002), supra.

BRIEF DESCRIPTION OF THE DRAWINGS

The figures show:

FIG. 13 shows by way of example a treatment plan for the tumour therapy according to the invention by injection of a tumour mRNA library, here in combination with GM-CSF, for patients with malignant melanoma. Autologous, stabilized RNA prepared from the patient's own tumour tissue is used for this. This amplified autologous tumour RNA is administered to the patient i.d. on days 0, 14, 28 and 42. In addition, one day after the RNA injection the patient is injected s.c. with GM-CSF (Leucomax® 100 µg/$m^2$ Novartis/Essex Pharma). Two weeks after the fourth injection (day 56), the response of the tumour is evaluated by a staging analysis (inter alia sonography, thorax X-ray, CT etc.) and by assessment of the immunological parameters induced by the therapy. When the course of the disease is stable or there is an objective tumour response (CR or PR), the patient receives in each case a further vaccination every four weeks. Further restaging analyses are carried out on day 126 and then at intervals of 12 weeks.

EXAMPLES

The following embodiment examples explain the present invention in more detail, without limiting it.

Example 1

Tumour Vaccination with RNA in an Animal Model

Materials and Methods

Figure 8:
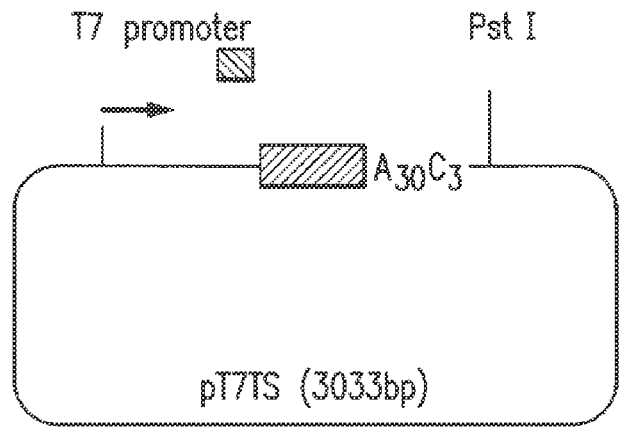
FIG. 8 shows a schematical view of the plasmid pT7TS, which was used for the in vitro transcription. Constructs according to the invention were cloned into the BglII and SpeI sites, the relative position of which to one another is shown. The region shaded in black contains the 5' untranslated region of the beta-globin gene from *Xenopus laevis*, while the region shaded in grey represents a corresponding 3' untranslated region of the beta-globin gene from *X. laevis* (SEQ ID NO: 4). The relative position of the T7 promoter (SEQ ID NO: 3), the PstI site used for sequencing, the poly($A^+$) tail ($A_{30}C_{30}$) and, with an arrow, the transcription direction are furthermore indicated.

Capped mRNA which codes for a shortened version of the Her-2/neu protein of the rat ("ECD-TM-neu-rat", containing the extracellular domain and the transmembrane region, but not the cytoplasmic region) was prepared, using the "SP6 mMessagemMachine" (Ambion), with the aid of a plasmid which substantially corresponded to the structure shown in FIG. 8, but contained an SP6 promoter instead of the T7 promoter and in which the ECD-TM-neu-rat construct was inserted after the SP6 RNA polymerase promoter. The mRNA prepared was dissolved in injection buffer (150 mM NaCl, 10 mM HEPES) at a concentration of 0.8 mg/l and the solution was mixed with protamine sulfate (Sigma) (1 mg protamine per 1 mg RNA). 50 µl of this solution were injected into the auriculae (in each case 25 µl per ear) of mice. Eight injections were performed, in each case one at the age of 6, 8, 13, 15, 20, 22, 27 and 29 weeks. Mice to which corresponding injections with injection buffer, with plasmid DNA which codes for ECD-TM-neu rat or with an antisense mRNA corresponding to the mRNA according to the invention were administered served as controls.

Results

Figure 1:
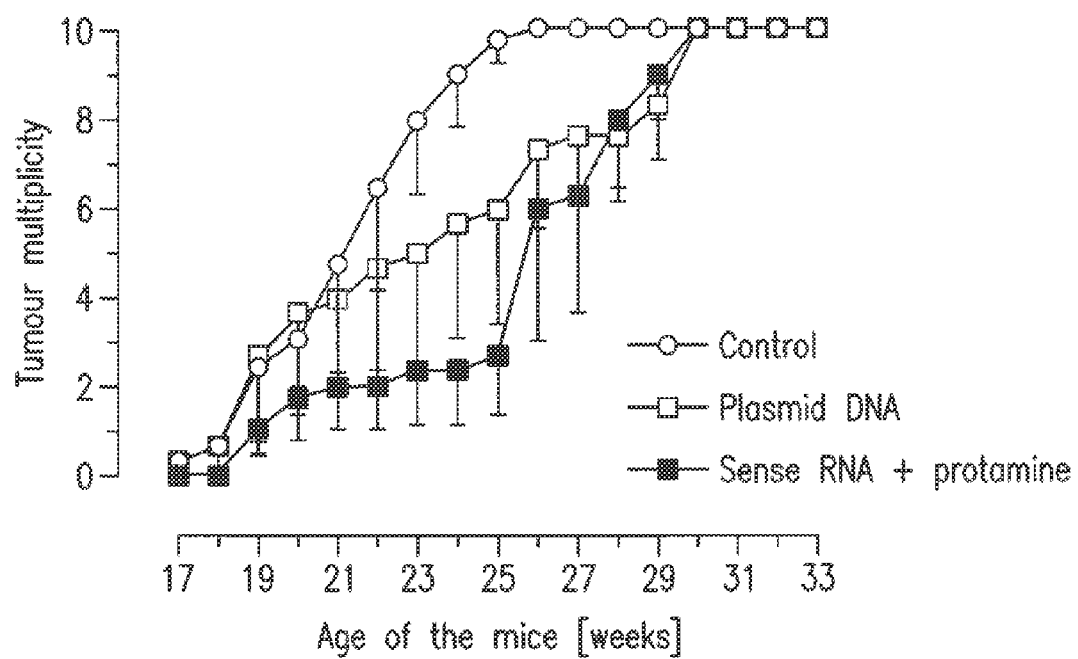
FIG. 1 shows a graphical view of the results of a tumour vaccination, with RNA, of mice (rat Her-2/neu transgenic animals) which develop mammary carcinomas spontaneously. The tumour multiplicity is plotted on the y-axis against the age of the mice on the x-axis. Untreated mice (n=4), which served as a control, all had tumours at an age of 6 months. Three mice were injected with DNA which codes for Her-2/neu, one mouse being tumour-free after 10 months. As a further negative control, 4 mice received an antisense mRNA complementary to the mRNA for Her-2/neu. These mice also all had tumours after 6 months (not shown). In contrast, one of 4 mice which were injected with mRNA which codes for Her-2/neu (i.e., the sense strand) was tumour-free after 9 months.
Figure 2:
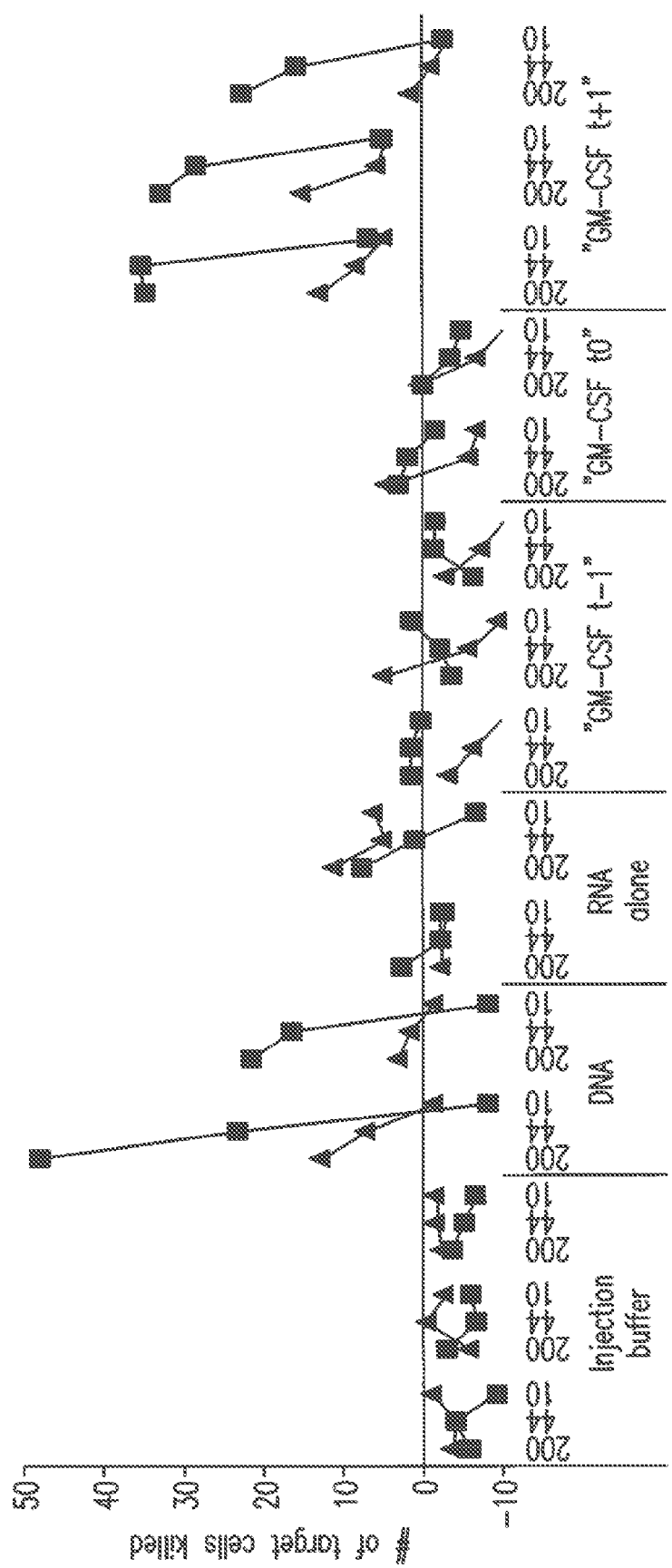
FIG. 2 shows a graphical view of the results of experiments relating to beta-galactosidase (beta-Gal)-specific CTL (cytotoxic T lymphocyte) activity by immunization with an mRNA which codes for beta-Gal, under the influence of GM-CSF. BALB/c mice were immunized with 25 µg of mRNA which codes for beta-Gal by injection into the inner auricula. The splenocytes were stimulated with beta-Gal protein in vitro and the CTL activity was determined 6 days after the in vitro stimulation using a standard $^{51}Cr$ release test. The target cells were P815 ($H_2^d$) cells which were charged (■) with the synthetic peptide TPHPARIGL, which corresponds to the $H_2^d$ epitope of beta-Gal, or were not charged (▲). In each case three or two animals were treated per group. Animals which were injected i.d. in both auriculae with only injection buffer served as a negative control. Animals which were injected i.d. in both auriculae with 10 µg of a plasmid which codes for beta-Gal in PBS served as a positive control ("DNA"). The test groups received RNA which codes for beta-Gal by itself or in combination with GM-CSF, which was injected 24 h ("GM-CSF t-1"), 2 h before the RNA injection ("GM-CSF t0") or 24 h after the RNA injection ("GM-CSF t+1") into the same site (into the auriculae) or at another site (s.c. on the back). In each case three different effector/target cell ratios (200, 44, 10) were tested.

Female BalB-neu T mice (BalB/c mice which express the oncogene Her-2/neu of the rat; cf. Rovero et al. (2000) J. Immunol. 165(9):5133-5142) which develop mammary carcinomas spontaneously were immunized with RNA which codes for a shortened version of the Her-2/neu protein ("ECD-TM-neu-rat", containing the extracellular domains and the transmembrane region, but not the cytoplasmic region). Four mice treated with injection buffer served as a negative control. A further group of three mice was injected with DNA which codes for the shortened Her-2/neu. Four mice received the mRNA which codes, according to the invention, for the tumour antigen Her-2/neu (shortened version of ECD-TM, see above). Four mice which were injected with the corresponding antisense RNA served as a further control group. As shown in FIG. 1, in the animals of the untreated control group a tumour multiplicity of on average 10 was observed after 26 weeks, whereby all animals having palpable breast tumours at the age of about 20 weeks. In contrast, in the case of immunization with the mRNA which codes for ECD-TM-neu-rat, a significant slowing down of the formation of carcinomas is to be observed, in particular a tumour multiplicity of 10 is achieved only at the age of 30 weeks. Furthermore, the size of the tumours is also reduced (not shown). Of the 4 mice treated with the mRNA according to the invention, one was still tumour-free after 9 months. That group of mice which had been injected with the antisense mRNA all showed tumours at the age of 6 months. The comparison group of mice injected with plasmid DNA which codes for the shortened version of Her-2/neu also showed a carcinoma formation which was slowed down compared with the untreated control group (cf. also in respect of corresponding plasmid DNA experiments on intramuscular injection: Di Carlo et al. (2001) Clin. Cancer Res. 7 (3rd supplement): 830s-837s), but the formation of carcinomas up to the 27th week was not slowed down to the same extent as in the case of immunization with mRNA according to the invention which codes for the shortened version of Her-2/neu. Furthermore, in the case of immunization with DNA, the abovementioned disadvantages, in particular the risk of integration of the DNA into the genome, the formation of anti-DNA antibodies etc., are to be taken into account.

Example 2

Influence of GM-CSF on RNA Vaccination

Materials and Methods
Mice
BALB-c AnNCrlBR (H-$2^d$) mice (female) 6-10 weeks old were obtained from Charles River (Sulzfeld, Germany).
Plasmids and Preparation of RNA
The ORF (LacZ) which codes for beta-galactosidase, flanked by 5'- and 3'-untranslated sequences from the beta-globin gene of *X. Laevis*, was into the plasmid pT7TS (P.A. Creek, Austin, Tex., USA), in order to prepare the plasmid pT7TS-kozak-5' beta gl-lacZ-3' beta gl-A30C30 (cf. Hoerr et al. (2000) Eur. J. Immonol. 30: 1-7). A schematical view of the general structure of the plasmid pT7TS with the flanking 5' and 3' untranslated sequences from the beta-globin gene of *X. Laevis* is shown in FIG. 8.

The plasmid prepared in this way was linearized with PstI and transcribed in vitro using the m-MessagemMachineT7 Kit (Ambion, Austin, Tex. USA). The RNA prepared in this way was purified by means of LiCl precipitation, phenol/chloroform extraction and ammonium acetate precipitation. Finally, the purified RNA was resuspended in injection buffer (150 mM NaCl, 10 mM HEPES) in a concentration of 0.5 mg/ml.
Media and Cell Culture
P815 and P13.1 cells were cultured in RPMI 1640 (Bio-Whittaker, Verviers, Belgium), supplemented with 10% heat-inactivated foetal calf serum (FCS) (PAN systems, Germany), 2 mM L-glutamine, 100 U/ml penicillin and 100 mg/ml streptomycin.

CTL cultures were kept in RPMI 1640 medium, supplemented with 10% FCS, 2 mM L-glutamine, 100 U/ml penicillin, 100 mg/ml streptomycin, 0.05 µM beta-mercaptoethanol, 50 mg/ml gentamycin, MEM non-essential amino acids (100×) and 1 mM sodium pyruvate. The CTL were restimulated for one week with 1 mg/ml beta-galactosidase protein (Sigma, Taufkirchen, Germany). On day 4, 4 ml of culture supernatant were carefully pipetted off and replaced by fresh medium containing 10 U/ml rIL-2 (final concentration).

Immunization
3 BALB/c mice per group were anesthetized with 20 mg pentobarbital i.p. per mouse. The mice were then injected i.d. in both auriculae with 25 mg of mRNA which codes for beta-galactosidase (beta-Gal) in injection buffer (150 mM NaCl, 10 mM HEPES). In some cases, granulocyte macrophage colony-stimulating factor (GM-CSF) was additionally injected into the same site or into an injection site away from this (into the auricula or s.c. into the back) 24 h or 2 h before or 24 h after the RNA injection. As a positive control, animals were injected i.d. in both auriculae with in each case 10 mg of a DNA plasmid which codes for beta-gal in PBS. A group of animals to which only injection buffer was administered i.d. into both auriculae served as a negative control. Two weeks after the first injection, a boost injection was performed in each case in the same manner as the first injection. Two weeks after the boost injection, blood was taken, the mice were sacrificed and the spleen was removed.
$^{51}$Cr Release Test
Splenocytes obtained from the spleen were stimulated with beta-gal protein in vitro and the CTL activity was determined after 6 days using a 6-hours $^{51}$Cr standard test as described in Rammensee et al. (1989) Immunogenetics 30: 296-302. Summarized briefly, target cells were marked with $^{51}$Cr and charged with the peptide TPHPARIGL for 20 min at room temperature. After co-incubation of effector and target cells (at in each case three different ratios of effector: target cells: 200, 44 and 10) in circular plates with 96 wells for 6 h, 50 ml of 200 ml of culture supernatant were pipetted into a Luma scintillation plate (Packard) with 96 wells and, after drying, the radioactivity was measured with a scintillation counter (1405 Microbeta Plus). The percentage specific release was determined from the amount of $^{51}$Cr released into the medium (A) minus the spontaneous release (B) divided by the total release (C) (using Triton X-100) minus the spontaneous release (B): Percent specific lysis=100 (A−B)/(C−B).
Cytokine ELISA
After 4 days of restimulation with beta-gal protein, the supernatant of the splenocyte culture was pipetted off and stored at −50° C. until used. 100 ml anti-mouse-anti-IFN-gamma or -IL-4 scavenger antibodies (Becton Dickenson, Heidelberg, Germany) were pipetted out overnight at 4° C. on MaxiSorb plates (Nalge Nunc International, Nalge, Denmark) at a concentration of 1 mg/ml in coating buffer (0.02% NaN$_3$, 15 mM Na$_2$CO$_3$, 15 mM NaHCO$_3$, pH 9.6). After washing three times with washing buffer (0.05% Tween 20 in PBS), the plates were saturated with 200 ml of blocking buffer (0.05% Tween 20, 1% BSA in PBS) for 2 h at 37° C. After washing three times with washing buffer, 100 ml of the cell culture supernatants were incubated for 5 h at 37° C. The plates were then washed four times with washing buffer, 100 ml of biotinylated anti-mouse-anti-IFN-gamma or -IL-4 detection antibodies (Becton Dickenson, Heidelberg, Germany) per well at a concentration of 0.5 mg/ml in blocking buffer were pipetted and incubation was carried out for 1 h at room temperature. After washing three times with washing buffer, 100 ml of a 1/1,000 dilution of streptavidin-HRP (BD Biosciences, Heidelberg, Germany) were added into each well. After 30 min at room temperature, the plates were washed three times with washing buffer and twice with bidistilled water. Thereafter, 100 ml of the ABTS substrate were added into each well. After 15-30 min at room temperature, the extinction at 405 nm was measured with a Sunrise ELISA reader (Tecan, Crailsheim, Germany).
Antibody ELISA
Two weeks after the boost injection, blood was taken from the mice via the orbital vein and blood serum was prepared.

100 ml of beta-gal protein at a concentration of 100 mg/ml in coating buffer (0.05 M Tris-HCl, 0.15 M NaCl, 5 mM $CaCl_2$, pH 7.5) were pipetted out for 2 h at 37° C. on to MaxiSorb plates (Nalge Nunc International, Nalge, Denmark). The plates were then washed three times with 200 ml of washing buffer (0.05 M Tris-HCl, 0.15 M NaCl, 0.01 M EDTA, 0.1% Tween 20, 1% BSA, pH 7.4) and saturated with protein with 200 ml of washing buffer overnight at 4° C. The plates were washed three times with washing buffer and blood sera were added in a dilution of 1/10, 1/30 or 1/90 in washing buffer. After 1 h at 37° C., the plates were washed three times with washing buffer and 100 ml of 1/1,000 dilutions of goat anti-mouse IgG1 or IgG2a antibodies (Caltag, Burlington, Calif., USA) were added. After 1 h at room temperature, the wells were washed three times with washing buffer and 100 ml of ABTS substrate per well were added. After 15-30 min at room temperature, the extinction at 405 nm was measured with a Sunrise ELISA reader (Tecan, Crailsheim, Germany).

Results and Discussion

Figure 3A:
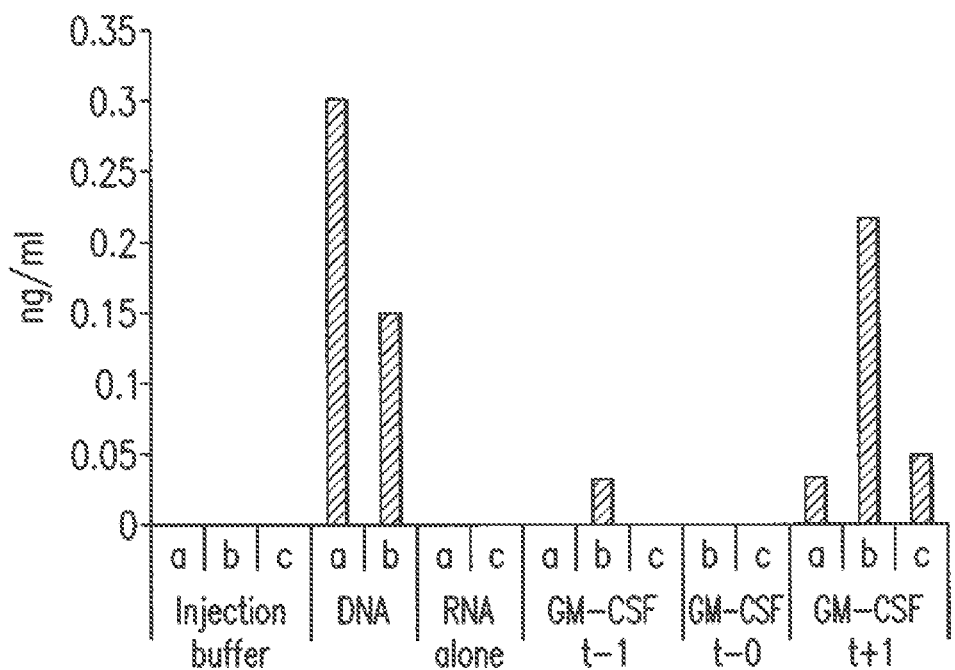
FIGS. 3A-3B show further graphical views of the results of ELISA standard tests specific for IFN-gamma (A) and IL-4 (B), which document the corresponding cytokine production of splenocytes which were restimulated with beta-Gal protein in vitro. BALB/c mice were immunized as already described above for FIG. 2. The splenocytes were stimulated with beta-Gal protein in vitro, the corresponding culture supernatants were obtained and the IFN-gamma or IL-4 concentration was determined using an ELISA standard test.
Figure 3B:
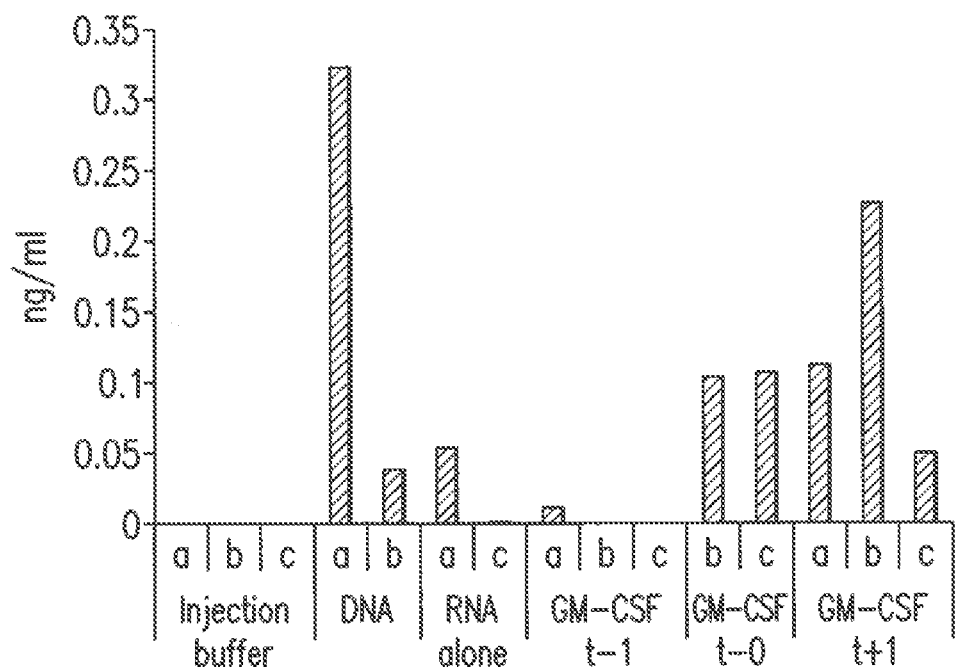
Figure 4A:
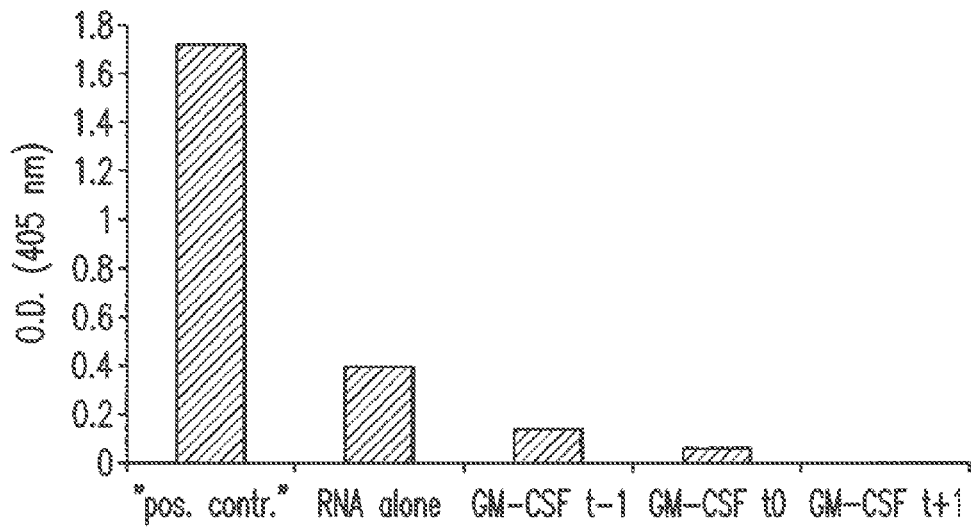
FIGS. 4A-4B show further graphical views which demonstrate the antibody response of mice immunized according to the invention. BALB/c mice were immunized as described for FIG. 2. Two weeks after the boost, blood was taken and the blood serum was obtained therefrom. Beta-Gal-specific IgG1 (A) and IgG2a antibodies (B) were determined with the aid of an ELISA test. In each case the extinction (OD) at 405 nm which results from the conversion of the substrate ABTS in the ELISA test is shown on the y-axis. The extinctions shown are the values from which the corresponding values of mice treated with injection buffer are subtracted.
Figure 4B:
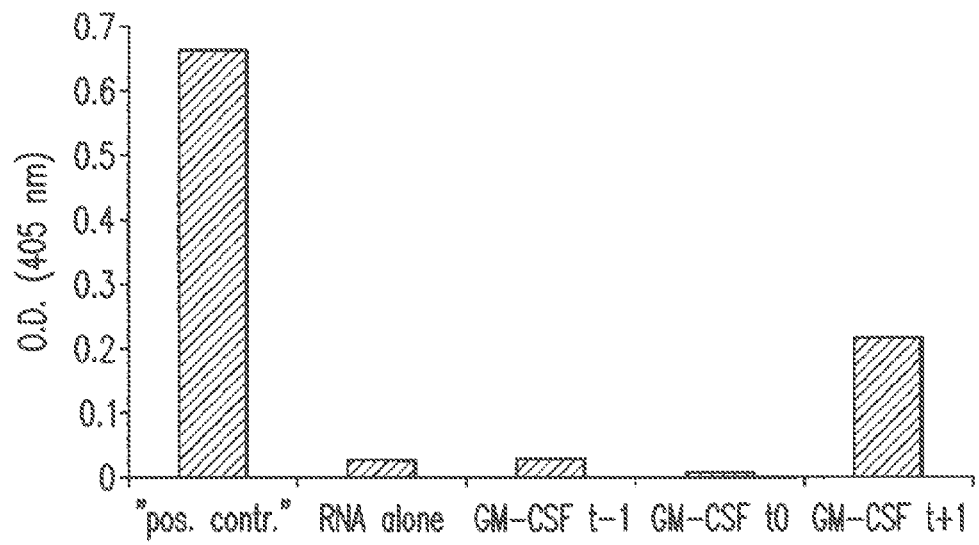

It was confirmed that direct injection of RNA which codes for beta-galactosidase into the auricula of mice induces an anti-beta-galactosidase immune response, substantially of the Th2 type. Production of anti-beta-galactosidase immunoglobulins of the IG1 type (FIG. 3A) and secretion of IL-4 (FIG. 3B) was found in splenocytes, stimulated with beta-galactosidase, from mice which had been injected with the RNA which codes for beta-galactosidase. To increase the efficiency of the RNA vaccine, the cytokine GM-CSF was additionally administered. This cytokine increases the efficiency of some DNA vaccines. It was furthermore found that the time of the GM-CSF injection influences the type of the immune response, compared with DNA injection (Kusakabe (2000) J. Immunol. 164: 3102-3111). It was found according to the invention that GM-CSF can enhance the immune response brought about by an RNA vaccination. The injection of GM-CSF one day before the injection of RNA shows scarcely any influence on the strength or the type of the immune response. In contrast, injection of GM-CSF 2 hours before injection of the RNA enhances the immune response (cf. the IL-4 release in FIG. 3B in the 2 mice injected with GM-CSF at time T=0), but does not influence the Th2 polarity. On the other hand, if GM-CSF is injected one day after the RNA vaccine into the same site or into a site away from this (not shown), not only is the immune response enhanced overall (cf. the antibody response according to FIG. 3), the immune response is polarized to the Th1 type (cf. the IFN-gamma production by splenocytes stimulated with beta-gal protein according to FIG. 3A, the production of IgG2a antibodies against beta-Gal according to FIG. 3B and the production of activated CTL according to FIG. 1). The injection of GM-CSF some minutes or some hours after the RNA injection should result in the same effect (enhancement and polarization) on the immune response.

Example 3

Effect of an RNase Inhibitor on mRNA Expression In Vivo

Figure 5:
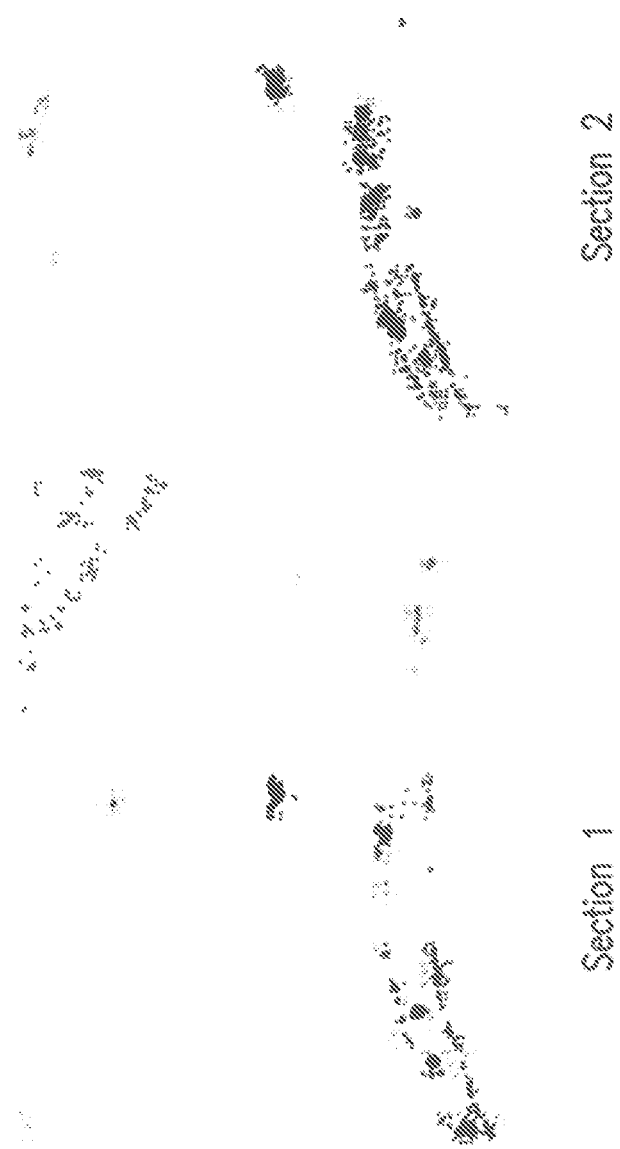
FIG. 5 shows microscope sections, stained with X-Gal, of the auricula of mice which have been injected i.d. into the auricula with mRNA which codes for beta-galactosidase. 12 hours after the injection of 25 µg RNA in HEPES-NaCl injection buffer, the ears were removed and sections stained with X-Gal were prepared. Blue cells indicate a beta-galactosidase activity. As can be seen from the two sections, only few blue cells are present.
Figure 6:
FIG. 6 shows a section, corresponding to FIG. 5, through an auricula of a mouse which was injected into the auricula with mRNA which codes for beta-galactosidase and was stabilized with protamine. The microscope section stained with X-Gal show a few cells stained blue.
Figure 7:
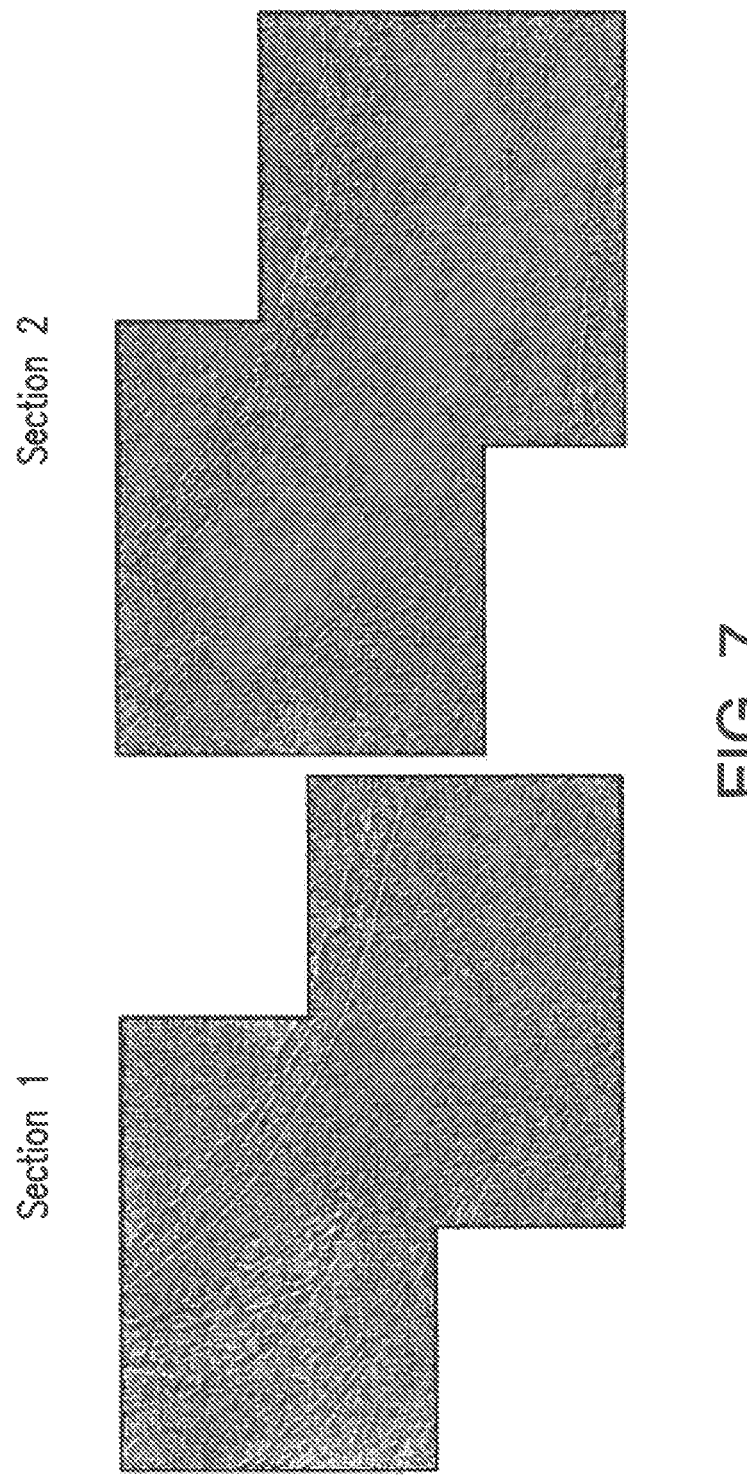
FIG. 7 shows two further sections through the auricula of mice, two images being produced per section in order to represent a larger area. In this case, mRNA which codes for beta-galactosidase, in a buffer, to which 10 U RNasin, an enzymatic RNase inhibitor from the pancreas (obtainable from Roche or Promega) was added directly before the injection, was injected into the auricula. Compared with the sections of FIG. 5 and FIG. 6, significantly more blue-stained regions of cells with beta-galactosidase activity are to be recognized.

Naked or protamine-associated or -complexed mRNA which codes for beta-galactosidase (prepared as described in example 2) was injected into the auricula of mice in an amount of 25 mg of RNA in injection buffer (150 mM NaCl, 10 mM HEPES). Further mice were injected with the mRNA which codes for beta-galactosidase, together with 10 U of the RNase inhibitor RNasin (an enzymatic RNase inhibitor extracted from the pancrease, obtainable from Roche or Promega). The RNase inhibitor was mixed with the RNA solution directly before the injection. After 12 hours, the ears were in each case removed from the mice. Thin microscope sections of the auriculae were prepared and were stained with X-gal. Injection of naked or protamine-associated mRNA leads to a detectable beta-galactosidase activity in a few cells in the corresponding thin sections (blue cells in FIGS. 5 and 6). Some cells have thus taken up the exogenous RNA here and translated it into the protein. When the mRNA which codes for beta-galactosidase was in the form protected with the RNase inhibitor RNasin, very many more blue cells were observed than in the case of the naked or protamine-associated RNA (FIG. 7). Since RNasin inhibits RNases, the half-life of the injected mRNA molecules in vivo is prolonged, where the environment (interstitial tissue) is contaminated with RNases. Such a stabilization of the RNA leads to an increased uptake by the surrounding cells and therefore to an increased expression of the protein coded by the exogenous RNA. This phenomenon can therefore also be utilized for an enhanced immune response to an antigen coded by the mRNA injected.

Example 4

RNA Vaccination of Patients with Malignant Diseases

Introduction

Cytotoxic T lymphocytes (CTL) recognize antigens as short peptides (8-9 amino acids) which are expressed bound to MHC class 1 glycoproteins on the cell surface (1). These peptides are fragments of intracellular protein molecules. However, there are indications that antigens taken up exogenously by macropinocytosis or phagocytosis can lead to the $CD8^+$ T cell-mediated immune response. The proteins are cleaved into proteosomes and the peptides formed by this means are transported out of the cytosol into the lumen of the endoplasmic reticulum and bound to MHC class I molecules.

The proteins processed in this way are transported as peptide/MHC class I complex to the cell surface and presented to the CTL. This process takes place in every cell and in this way makes it possible for the immune system to monitor accurately each individual cell for the presence of proteins which are foreign to the body or modified or embryonic, regardless of whether they originate from intracellular pathogenic germs, oncogenes or dysregulated genes. By this means, cytotoxic lymphocytes are capable of recognizing and lysing infected and neoplastic cells, respectively (2, 3).

In recent years various tumour-associated antigens (TAA) and peptides which are recognized by CTL and therefore lead to lysis of tumour cells have been successfully isolated (21-27). These TAA are capable of stimulating T cells and inducing antigen-specific CTL, if they are expressed as a complex of HLA molecule and peptide on antigen-presenting cells (APC).

In numerous studies carried out mainly on patients with malignant melanoma, it has been possible to demonstrate that malignant cells lose the expression of TAA as the tumour disease proceeds. Similar circumstances are also observed with vaccinations with individual tumour antigens. Under vaccination therapies, selection of tumour cells may also occur, which renders possible an escape from the immune system and a progression of the disease in spite of therapy. The use of several different tumour antigens as envisaged in the treatment plan according to the invention of the present example should prevent selection of tumour cells and escape of the malignant cells from the immune system due to loss of antigens.

A method with which DC can be transfected with RNA from a plasmid which codes for a tumour antigen has recently been developed (Nair et al., 1998, Nair et al., 2000). Transfection of DC with RNA for CEA or telomerase led to induction of antigen-specific CTL. This process renders it possible to induce CTL and T helper cells against several epitopes on various HLA molecules from a tumour antigen. A further advantage of this strategy is the fact that neither the characterization of the tumour antigens or epitopes used nor definition of the HLA haplotype of the patient is a prerequisite. By a polyvalent vaccine of this type, the probability of the occurrence of so-called clonal "tumour escape" phenomena could be reduced significantly. Furthermore, T cell-mediated immune responses against antigens processed and presented by the natural route and with possibly a higher immune dominance could be induced by this approach. By additional participation of MHC class II-restricted epitopes, the induced tumour-specific immune response could be enhanced and maintained for longer.

A treatment scheme according to the invention for tumour vaccination of patients with advanced malignant diseases (mammary, ovarian, colorectal, pancreatic and renal cell carcinomas) is provided by way of example. In this, RNA which has been prepared from plasmids which code for MUC1, Her-2/neu, telomerase and MAGE-1 tumour antigens and influenza matrix protein (IMP) (positive control) is administered intradermally to patients with the abovementioned malignant diseases. A CTL induction in vivo is thereby rendered possible, in order to prevent the progression of the disease or to effect the regression thereof in this way. The tumour antigens mentioned are expressed on the malignant cells of mammary, ovarian, colorectal, pancreatic and renal cell carcinomas.

According to the treatment plan (cf. the following statements in this respect and FIG. 9), the RNA species prepared in the laboratory which code for CEA, MUC1, Her-2/neu, telomerase, Mage-1 and IMP are administered to the patient i.d., initially 4× on days 0, 14, 28 and 42. In addition, GM-CSF (Leucomax®, 100 µg/m$^2$, Novartis/Essex Pharma) is administered s.c. to the patient in each case one day after the RNA inoculation.

The treatment according to the invention is an immunisation approach which requires only minimal interventions on the patient (injection). Therapy is conducted ambulant and is suitable for many tumour patients, without the limitation to particular HLA types or defined T cell epitopes. Furthermore, polyclonal CD4$^+$-T helpers and also CD8$^+$-CTL can be induced by this therapy.

Treatment Plan

The RNAs for several tumour antigens (MUC1, Her-2/neu, telomerase, MAGE-1) and for a control antigen, influenza matrix protein (IMP, a viral antigen) are administered i.d. to the patient on days 0, 14, 28 and 42. In addition, the patients receive GM-CSF (Leucomax® (100 µg/m$^2$) Novartis/Essex Pharma) s.c. in each case one day after the RNA inoculation. When the course of the disease is stable or there is an objective tumour response (complete remission (CR) or partial remission (PR)), where appropriate the patients receive the vaccinations s.c. once a month. After the fourth injection (day 49), the response of the tumour is evaluated radiologically, by laboratory chemistry and/or sonographically, and the immunological phenomena induced by the therapy are evaluated.

From day 70, the immunization therapy is continued at intervals of 4 weeks.

On days 0, 14, 28, 42 and 49, in each case blood samples are taken for laboratory parameters, Diff-BB, FACS analysis and cytokines (50 ml in total). Restaging of the patients takes place from day 49 and where appropriate every further 4 to 8 weeks.

Figure 9:
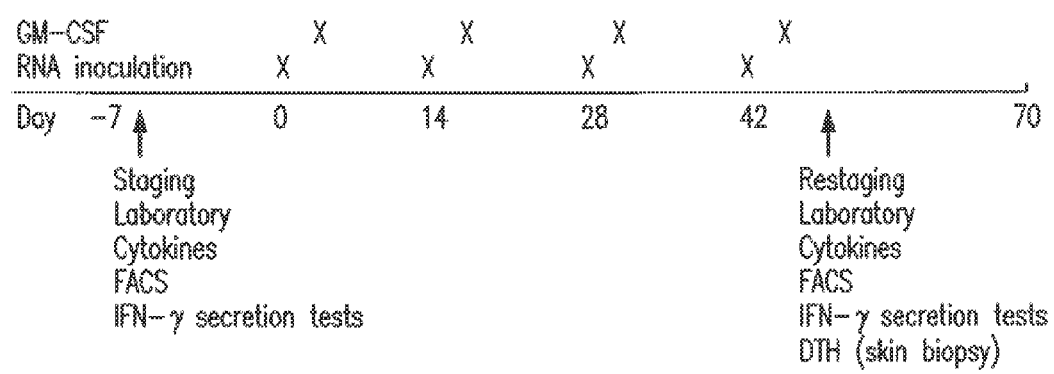
FIG. 9 shows in a flow chart, by way of example, the course of an RNA vaccination therapy according to the invention with assisting administration of GM-CSF. The mRNA molecules which code for one or more tumour antigens (MUC1, Her-2/neu, tilomerase, MAGE-1) or a mRNA which codes for a control antigen (influenza matrix protein (IMP), a viral antigen) are administered i.d. to the patient on days 0, 14, 28 and 42. In addition, one day after the RNA inoculation the patient is injected s.c. with GM-CFS (Leucomax® (100 µg/$m^2$) from Novartis/Essex Pharma). When the course is stable or there is an objective tumour response (complete remission (CR) or partial remission (PR)), the patients receive the vaccinations s.c. once a month. After the fourth injection (day 49), the response of the tumour is evaluated radiologically, by laboratory chemistry or sonographically, and the immunological phenomena induced by the therapy are evaluated. From day 70, the immunization therapy is continued at intervals of 4 weeks. On day 0, 14, 28, 42 and 49, blood samples are taken for determination of appropriate laboratory parameters, the differential blood count (Diff-BB), FACS analysis and cytokines. Restaging of the patient takes place from day 49 and where appropriate every further 4 to 8 weeks.

The treatment plan is shown schematically in FIG. 9.

Laboratory: clotting, electrolytes, LDH, β2-M, CK, liver enzymes, bilirubin, creatinine, uric acid, total protein, CRP, tumour markers (Ca 12-5, Ca 15-3, CEA, Ca 19-9): 15 ml of blood.

Diff-BB: differential blood count with smear (5 ml of EDTA blood).

Cytokines: 10 ml of serum

FACS: 10 ml of heparin blood.

ELIspot: 20 ml of heparin blood.

Multitest: analysis of the DTH reaction.

DTH: ("delayed type hypersensitivity", delayed T cell-mediated reaction) analysis of the reaction to intradermally administered RNA. In addition a skin biopsy should be performed in the event of a positive DTH reaction (local anaesthesia is not necessary for this).

Preparation of RNA from Plasmids

For production of a vaccine based on mRNA, only precursors which are chemically synthesized and purified from bacteria are required. This is preferably effected in a specially equipped RNA production unit. This is in a sealed-off room which is declared an RNase-free zone, i.e. work with RNase (e.g. purification of plasmids) must not be carried out. Contamination with naturally occurring RNases is also constantly checked. This room is fitted out with new apparatuses (4° C. and –20° C. refrigerators, heating block, sterile bench, centrifuges, pipettes) which have never been used for biological or clinical work. This RNA production unit is used exclusively for enzymatic production (in vitro transcription) of mRNA (without bacterial, viral or cell culture work). The end product comprises a sterile RNA solution in HEPES/NaCl buffer. Quality analyses are carried out on a formaldehyde-agarose gel. In addition, the RNA concentration and the content of proteins are determined photometrically ($OD_{320}$<0.1; ratio of $OD_{260}$/$OD_{280}$>1.8 in pure RNA). Possible contamination by LPS is analysed in the LAL test. All RNA samples are subjected to sterile filtration before administration.

Plasmid Constructs

The chosen genes (CEA, mucin1, Her-2/neu, telomerase, Mage-A1 and influenza matrix) are amplified via a PCR using a heat-stable high-performance enzyme (pfu, Stratagene). The genes originate from tumour cDNA (mucin1, Her-2/neu, telomerase), or they have been cloned into bacterial vectors (influenza matrix and MAGE-A1). The PCR fragments are cleaved with restriction enzymes (mucin1: BglII-SpeI; Her-2/neu: HinDIIIblunt-SpeI; telomerase: BglII-SpeI; MAGE-A1: BamHI-SpeI; influenza matrix protein: BglII-SpeI) and cloned into the T7TS-Plasmid (cf. FIG. 8) via the BglII and SpeI restriction sites. Plasmids of high purity are obtained via the Endo-free Maxipreparation Kit (Qiagen, Hilden, Germany). The sequence of the vector is controlled via a double-strand sequencing from the T7 promoter up to the PstI site and documented. Plasmids with a correct inserted gene sequence without mutations are used for the in vitro transcription. (Control via the published sequences: Accession Numbers: M11730 for Her-2/neu, NM_002456 for MUC1, NM_003219 for telomerase TERT, V01099 for influenza matrix and M77481 for MAGE-A1).

In Vitro Transcription
Production of Linear, Protein Free DNA

500 µg of each plasmid are linearized in a volume of 0.8 ml via digestion with the restriction enzyme PstI in a 2 ml Eppendorf reaction vessel. This cleaved construct is transferred into the RNA production unit. 1 ml of a mixture of phenol/chloroform/isoamyl alcohol is added to the linearized DNA. The reaction vessel is vortexed for 2 minutes and centrifuged at 15,000 rpm for 3 minutes. The aqueous phase is removed and mixed with 0.7 ml 2-propanol in a 2 ml reaction vessel. This vessel is centrifuged at 15,000 rpm for 15 minutes, the supernatant is discarded and 1 ml 75% ethanol is added. The reaction vessel is centrifuged at 15,000 rpm for 10 minutes and the ethanol is removed. The vessel is centrifuged for a further 2 minutes and the residues of the ethanol are removed with a microliter pipette tip. The DNA pellet is then dissolved in 1 µg/ml in RNase-free water.

Enzymatic Synthesis of the RNA

The following reaction mixture is prepared in a 50 ml Falcon tube: 100 µg linearized protein-free DNA, 1 ml 5× buffer (200 mM Tris-HCl (pH 7.9), 30 mM $MgCl_2$, 10 mM spermidine, 50 mM NaCl, 50 mM DTT), 200 µl ribonuclease (RNase) inhibitor (recombinant, 5,000 U), 1 ml rNTP mix (in each case 10 mM ATP, CTP, UTP; 2 mM GTP), 1 ml CAP analogue (8 mM), 150 µl T7 polymerase (3,000 U) and 2.55 ml RNase-free water. The total volume is 5 ml. The mixture is incubated at 37° C. for 2 hours in a heating block. Thereafter, 100 U of RNase-free DNase are added and the mixture is incubated again at 37° C. for 30 minutes. The DNA matrix is enzymatically degraded by this procedure.

Description and Origin of the Individual Components

T7 polymerase: purified from an *E. coli* strain which contains a plasmid with the gene for the polymerase. This RNA polymerase uses as the substrate only promoter sequences of the T7 phage; Fermentas.

NTPs: synthesized chemically and purified via HPLC. Purity more than 96%; Fermentas.

CAP analogue: synthesized chemically and purified via HPLC. Purity more than 90%; Institute of Organic Chemistry of the University of Tübingen.

RNase inhibitor: RNasin, for injection, prepared recombinantly (*E. coli*); Promega.

DNase: Pulmozym® ("dornase alfa"); Roche

Purification

The RNA treated with DNase is mixed with 20 ml of a solution of 3.3 ml 5 M $NH_4OAc$ plus 16.65 ml of ethanol. The mixture is incubated at −20° C. for 1 hour and centrifuged at 4,000 rpm for 1 hour. The supernatant is removed and the pellet is washed with 5 ml of 75% RNase-free ethanol. The vessel is centrifuged again at 4,000 rpm for 15 minutes and the supernatant is removed. The vessel is centrifuged again under the previous conditions and the ethanol which remains is removed with a microliter pipette tip. The reaction vessel is opened and the pellet is dried under a sterile bench in the sterile environment.

1 ml of RNase-free water is added to the dried RNA. The pellet is incubated at 4° C. for at least 4 hours. 2 µl of the aqueous solution are subjected to a quantitative analysis (determination of the UV absorption at 260 nm). 2 ml of a phenol/chloroform/isoamyl alcohol solution are added to 1 ml of aqueous RNA solution. The mixture is vortexed for 2 minutes and centrifuged at 4,000 rpm for 2 minutes. The aqueous phase is removed with a microliter pipette and transferred into a new reaction vessel. 4 ml of a solution of 0.66 ml 5 M $NH_4OAc$ plus 3.33 ml ethanol are added. The mixture is incubated at −20° C. for 1 hour and centrifuged at 4,000 rpm for 1 hour. The supernatant is removed and the pellet is washed with 75% RNase-free ethanol. The vessel is centrifuged again at 4,000 rpm for 15 minutes and the supernatant is removed. The vessel is centrifuged again under the previous conditions and the ethanol which remains is removed with a microliter pipette tip. The reaction vessel is opened and the pellet is dried under a sterile bench in the sterile environment.

The RNA is dissolved in RNase-free water and adjusted to a concentration of 10 mg/ml. It is incubated for 12 hours at 4° C. A final concentration of 2 mg/ml is achieved by addition of injection buffer (150 mM NaCl, 10 mN HEPES). The end product is preferably subjected to sterile filtration under GMP conditions before use.

Application of the RNA

Each patient receives at two different sites an intradermal (i.d.) injection of in each case 150 µl of the injection solution in which in each case 100 µg of antigen-coding mRNA (CEA, Her-2/neu, MAGE-A1, mucin 1, telomerase, influenza matrix protein) are present in solution.

After the primary immunization, a booster immunization is carried out every 14 days, for the inoculations then to be repeated at a monthly interval. In each case one day after the RNA injection, GM-CSF (Leucomax®, Sandoz/Essex Pharma) is administered subcutaneously (s.c.) to the patient.

If a clinical response is present or the disease is stabilized, this therapy is continued at monthly intervals.

Further Immunological Investigations In Vitro (Optional)

Flow cytometry analyses of PBMC for quantification of CTL precursors;

$^{51}Cr$ release tests;

Soluble receptor and cytokine levels in the serum;

DTH reaction (skin reaction to intradermally injected RNA, "delayed type hypersensitivity", T lymphocyte-mediated reaction); and Skin biopsy samples from the injection site for histological analysis for T cell infiltration (pathology).

Parameters for Evaluation of the Efficacy

To be able to answer the question of the efficacy of this immunotherapy, the induction of tumour-specific T cells and a measurable tumour remission is used. Parameters are T cell reactions measured in vitro and in vivo and changes in the size of bidimensionally recordable tumour manifestation or laboratory chemistry parameters of the course of the disease.

Objective remission is defined as the best response in the form of a complete or partial remission, corresponding to the criteria listed below. The remission rate is calculated from the ratio of the number of patients with objective remission and the total number of evaluable patients.

A change in the immune status, determined by immunotyping of peripheral mononuclear cells, an increase in the antigen-specific CTL precursor frequency in the peripheral blood and the induction of a persistent tumour-specific T cell activity are assessed as the immunological response to the therapy. For this purpose, in vitro induction cultures are established for activation of tumour-specific CTL.

Remission Criteria (acc. to UICC)

Complete remission (CR): Complete regression of all measurable tumour manifestation, documented by 2 control investigations at least 4 weeks apart.

Partial remission (PR): Decrease in size of the total area dimensions (product of two tumour diameters or linear measurement of one-dimensionally measurable lesions of all tumour findings by 50% for at least 4 weeks). No new occurrence of tumour manifestations or progression of a tumour finding.

"No Change" (NC): Decrease of all the measurable tumour manifestations by less than 50% or increase in a tumour finding.

Progression (PD): Increase in size of the tumour parameters in at least one focus or new occurrence of a tumour manifestation.

REFERENCES

1. Rammensee H G, Falk K, Rotzschke O: Peptides naturally presented by MHC class I molecules. Annu Rev Immunol 11: 213, 1993.
2. Bevan M. J: Antigen presentation to cytotoxic T lymphocytes in vivo. J Exp Med 182: 639, 1995.
3. Rock K. L: A new foreign policy: MHC class I molecules police the outside world. Immunol Today 17:131, 1996.
4. Steinman, A. M: The dendritic cell system and its role in immunogenicity. Annu. Rev Immunol 9:271, 1991.
5. Steinman R M, Witmer-Pack M, Inaba K: Dendritic cells: antigen presentation, accessory function and clinical relevance. Adv Exp Med Biol 329:1, 1993.
6. Inaba K, Metlay J P, Crowley M T, Steinman R M: Dendritic cells pulsed with protein antigens in vitro can prime antigen-specific, MHC-restricted T cells in situ. J Exp Med 172:631, 1990.
7. Austyn J M: New insight into the mobilisation and phagocytic activity of dendritic cells. J Exp Med 183: 1287, 1996.
8. Romani N, Koide S, Crowley M, Witmer-Pack M, Livingstone A M, Fathman C G, Steinman R M: Presentation of exogenous protein antigens by dendritic cells to T cell clones. J Exp Med 169:1169, 1989.
9. Nair S, Zhou F, Reddy R, Huang L, Rouse B T: Soluble proteins delivered to dendritic cells via pH-sensitive liposomes induce primary cytotoxic T lymphocyte responses in vitro. J Exp Med 175:609, 1992.
10. Cohen P J, Cohen P A, Rosenberg S A, Katz S I, Mule J J: Murine epidermal Langerhans cells and splenic dendritic cells present tumor-associated antigens to primed T cells. Eur J Immunol 24:315, 1994.
11. Porgador A, Gilboa E: Bone-marrow-generated dendritic cells pulsed with a class I-restricted peptide are potent inducers of cytotoxic T lymphocytes. J Exp Med 182:255, 1995.
12. Celluzzi C M, Mayordomo J I, Storkus W J, M. T. Lotze M T, and L. D. Falo L D: Peptide-pulsed dendritic cells induce antigen-specific, CTL-mediated protective tumor immunity. J Exp Med 183:283, 1996.
13. Zitvogel L, Mayordomo J I, Tjandrawan T, DeLeo A B, Clarke M R, Lotze M T, Storkus W J: Therapy of murine tumors with tumor peptide-pulsed dendritic cells: dependence on T cells, B7 costimulation, and T helper cell 1-associated cytokines. J Exp Med 183:87, 1996.
14. Porgador A, Snyder D, Gilboa E: Induction of antitumor immunity using bone marrow-generated dendritic cells. J Immunol 156:2918, 1996.
15. Paglia P, Chiodoni C, Rodolfo M, Colombo M P: Murine dendritic cells loaded in vitro with soluble protein prime cytotoxic T lymphocytes against tumor antigen in vivo. J Exp Med 183:317, 1996.
16. Brossart P, Goldrath A W, Butz E A, Martin S, Bevan M J: Adenovirus mediated delivery of antigenic epitopes into DC by a means of CTL induction. J Immunol 158: 3270, 1997.
17. Fisch P, Köler G, Garbe A, Herbst B, Wider D, Kohler H, Schaefer H E, Mertelsmann R, Brugger W, Kanz L: Generation of antigen-presenting cells for soluble protein antigens ex vivo from peripheral blood CD34+hematopoetic progenitor cells in cancer patients. Eur J Immunol 26: 595, 1996.
18. Sallusto F, Cella M, Danieli C, Lanzavecchia A: Dendritic cells use macropinocytosis and the mannose receptor to concentrate macromolecules in the Major Histocompatibility Complex class II compartment: Down regulation by cytokines and bacterial products. J Exp Med 182:389, 1995.
19. Bernhard H, Disis M L, Heimfeld S, Hand S, Gralow J R, Cheever M A: Generetion of immunostimulatory dendritic cells from human CD34+ hematopoetic progenitor cells of th bone marrow and peripheral blood. Cancer Res 55: 1099, 1995.
20. Hsu F J, Benike C, Fagnoni F, Liles T M, Czerwinski D, Taidi B, Engelman E G, Levy R: Vaccination of patients with B-cell lymphoma using autologous antigen-pulsed dendritic cells. Nat Med 2: 52, 1996.
21. Robbins P F, Kawakami Y: Human tumor antigens recognized by T cells. Curr Opin Immunol 8: 628, 1996.
22. Linehan D C, Goedegebuure P S, Peoples G E, Rogers S O, Eberlein T J: Tumor-specific and HLA-A2 restricted cytolysis by tumor-associated lymphocytes in human metastatic breast cancer. J Immunol 155: 4486, 1995.
23. Peoples G E, Goedegebuure P S, Smith R, Linehan D C, Yoshino I, Eberlein T J: Breast and ovarian cancer specific cytotoxic T lymphocytes recognize the same HER-2/-neu derived peptide. Proc Natl Acad Sci USA 92: 432, 1995.
24. Fisk B, Blevins T L, Wharton J T, Ioannides C G: Identification of an immunodominant peptide of HER-2/neu protooncogene recognized by ovarian tumor-specific cytotoxic t lymphocyte lines. J Exp Med 181: 2109, 1995.
25. Brossart P, Stuhler G, Flad T, Stevanovic S, Rammensee H-G, Kanz L and Brugger W. HER-2/neu derived peptides are tumor-associated antigens expressed by human renal cell and colon carcinoma lines and are recognized by in vitro induced specific cytotoxic T lymphocytes. Cancer Res. 58: 732-736, 1998.
26. Apostolopoulos, V. and McKenzie, I. F. C., Cellular mucins: targets for immunotherapy. Crit. Rev. Immunol. 14: 293-302, 1995.
27. Brossart P, Heinrich K S, Stevanovic S, Stuhler G, Behnke L, Reichardt V L, Muhm A, Rammensee H-G, Kanz L, Brugger W. Identification of HLA-A2 restricted T cell epitopes derived from the MUC1 tumor antigen for broadly applicable cancer vaccines. Blood 93: 4309-4317, 1999
28. Brossart P, Wirths S, Stuhler G, Reichardt V L, Kanz L, Brugger W. Induction of CTL responses in vivo after vaccinations with peptide pulsed dendritic cells. Blood 96:3102-8, 2000
29. Kugler A, Stuhler G, Walden P, Zoller G, Zobywalski A, Brossart P, Trefzer U, Ullrich S, Müller C A, Becker V, Gross A J, Hemmerlein B, Kanz L, Müller G A, Ringert R H. Regression of human metastatic renal cell carcinoma after vaccination with tumor cell-dendritic cell hybrids. Nature Med 3: 332-336, 2000 (IF 25,58)
30. Nestle F O, Alijagic S, Gilliet M, Sun Y, Grabbe S, Dummer R, Burg G, Schadendorf D (1998) Vaccination of melanoma patients with peptide- or tumor lysate-pulsed dendritic cells. Nat. Med. 4:328
31. Schuler-Thurner B, Dieckmann D, Keikavoussi P, Bender A, Maczek C, Jonuleit H, Roder C, Haendle I, Leisgang W, Dunbar R, Cerundolo V, von Den D P, Knop J, Brocker E B, Enk A, Kampgen E, Schuler G (2000) Mage-3 and influenza-matrix peptide-specific cytotoxic T cells are inducible in terminal stage HLA-A2.1+ melanoma patients by mature monocyte-derived dendritic cells. J. Immunol. 165:3492

32. Thurner B, Haendle I, Roder C, Dieckmann D, Keikavoussi P, Jonuleit H, Bender A, Maczek C, Schreiner D, von Den D P, Brocker E B, Steinman R M, Enk A, Kampgen E, Schuler G (1999) Vaccination with mage-3A1 peptide-pulsed mature, monocyte-derived dendritic cells expands specific cytotoxic T cells and induces regression of some metastases in advanced stage IV melanoma. J. Exp. Med. 190:1669

Example 5

Vaccination with Autologous, Amplified Tumour RNA in Patients with Malignant Melanoma Introduction The incidence of malignant melanoma has increased sharply worldwide in recent years. If the melanoma disease is already in the metastased stage at the time of diagnosis, there is currently no therapy which has a positive influence on the further course of the disease with sufficient certainty.

Vaccination therapies carried out to date using dendritic cells are very labour-, cost- and time-intensive because of the complicated culturing of the cells (GMP conditions). Furthermore, the studies have hitherto concentrated predominantly on known tumour-associated antigens (TAA), such as, for example, melan-A or tyrosinase.

A number of various immunological phenomena, such as, inter alia, the occurrence of spontaneous tumour regressions or spontaneous involution of metastases, have made the melanoma the prior candidate for testing immunotherapy investigations (Parkinson et al., 1992). In addition to experiments on non-specific stimulation of the immune system by means of interleukin-2, mistletoe extracts, BCG and interferons, which have so far not led to decisive breakthroughs in the therapy of advanced tumour diseases, the strategy of induction of various highly specific cytotoxic T lymphocytes (CTL) has been pursued in particular in recent years. These CTL are capable of recognizing and killing autologous melanoma cells (Boon et al., 1994; Houghton, 1994). Studies of this process have shown that the CTL recognize defined peptides in combination with MHC class I molecules. The presentation of peptides by antigen-presenting cells (APC) is the physiological route to generation of specific immune responses by lymphocytes (Rammensee, 1993). Dendritic cells have proved to be potent antigen-presenting cells which lead to an induction of the immune response by two routes: The first is the direct presentation of peptides towards CD8$^+$-T lymphocytes and activation thereof (Schuler & Steinmann, 1985; Inaba et al., 1987; Romani et al., 1989), and the second is the generation of a protective immune response, which is mediated by CD4$^+$ helper lymphocytes, and requires a presentation of peptides via MHC class II molecules (Grabbe et al., 1991, 1992, 1995).

By means of peptide analysis, it was therefore possible to identify in this way various tumour-associated antigens (TAA) which are specific for the melanoma and, after presentation in combination with the MHC molecule and recognition by the CTL, lead to cytolysis of the tumour cells (Schadendorf et al., 1997, p. 21-27).

The use of autologous, dendritic cells was tested in the context of a pilot study on melanoma patients in respect of its potential to induce cytotoxic T lymphocytes effectively, rapidly and reliably. In this study, 16 melanoma patients in stage IV who had already been pretreated by chemotherapy were vaccinated with peptide-charged dendritic cells. The response rates were above 30% (5/16 patients) (Nestle et al., 1998). In a further independent study it was possible to demonstrate an even higher response rate of more than 50% (6/11 patients) after immunization of melanoma patients who had already been pretreated by chemotherapy with MAGE-3A1-charged dendritic cells (Thurner et al., 1999). A significant expansion of MAGE-A3-specific CD8$^+$-T cells was also observed in 8/11 patients. A regression of the metastases took place in some cases after the DC vaccination. This was accompanied by a CD8$^+$-T cell infiltration. This showed that the T cells induced were active in vivo. A disadvantage of this strategy is the high outlay on costs and the laboratory (in particular GMP conditions). Large amounts of blood from the patient are required for the time-intensive generation of the DC. In the preparation of the peptides, on the one hand only known tumour-associated antigens can be used, and on the other hand various peptides are necessary, depending on the HLA haplotype.

A further development of this approach is vaccination with RNA-transfected DC (Nair et al., 1998, Nair et al., 2000). In the meantime, numerous studies demonstrate that DC from mice and humans which have been transfected with mRNA can induce an efficient CTL response in vitro and in vivo and can lead to a significant reduction in metastases (Boczkowski et al., 1996, 2000; Ashley et al., 1997; Nair et al., 1998, 2000; Heiser et al., 2001; Mitchell and Nair, 2000; Koido et al., 2000; Schmitt et al., 2001). A great advantage in the use of RNA compared with peptides is that the most diverse peptides can be processed and presented from one mRNA which codes for a TAA. By a polyvalent vaccine of this type, the probability of the occurrence of so-called clonal "tumour escape" phenomena can be reduced significantly. Furthermore, T cell-mediated immune responses against antigens processed and presented by the natural route and with potentially a higher immune dominance can be induced by this system. By additional participation of MHC class II-restricted epitopes, the tumour-specific immune response induced can be intensified and maintained for longer. Nevertheless, this process also can be carried out only with a high outlay on the laboratory (GMP conditions) because of the necessary culturing of the autologous DCs.

In the present strategy according to the invention, vaccination is carried out with the RNA expression profile present in the autologous tumour of the patient. The specific tumour profile of the patient is thereby taken into account, unknown TAAs also being included in the inoculation. Expensive culture of the DCs is omitted, since RNAs (not transfected DCs) are used in the vaccination.

A vaccination therapy using amplified autologous tumour RNA on patients with metastased malignant melanoma, in particular stage III/IV, is therefore provided according to the invention. Tumour-specific cytotoxic T cells are induced in vivo by the vaccination, in order thus to achieve a clinico-therapeutic effect (tumour response). This is an immunisation system which requires only minimal interventions on the patient (injection). Therapy can be conducted ambulant and is suitable for many tumour patients, without the limitation to particular HLA types or defined T cell epitopes. Furthermore, polyclonal CD4$^+$-T helpers and also CD8$^+$-CTL can be induced by this therapy. From the point of view of the strategy, it is decisive also that hitherto unknown TAAs are taken into account in the vaccination protocol, and the exclusive use of autologous material is particularly advantageous.

Treatment Plan

The amplified autologous tumour RNA is administered to the patient i.d. on days 0, 14, 28 and 42. In addition, the patients receive GM-CSF (Leucomax® 100 µg/m², Novartis/Essex) s.c. in each case one day after the RNA inoculation. Each patient receives, at two different sites, an i.d. injection of in each case 150 µl of the injection solution, in which in each case 100 µg of autologous tumour RNA is dissolved.

2 weeks after the fourth injection (day 56), where appropriate the response of the tumour is evaluated by a staging analysis (inter alia sonography, thorax X-ray, CT etc.; in this context see the statements below) and by assessment of the immunological parameters induced by the therapy.

When the course of the disease is stable or there is an objective tumour response (CR or PR), the patients receive the vaccinations every four weeks. Further restaging analyses can be envisaged e.g. on day 126 and then at an interval of 12 weeks.

A diagram of the treatment plan is shown in FIG. 13.

Preparation of Autologous Tumour RNA

Figure 10:
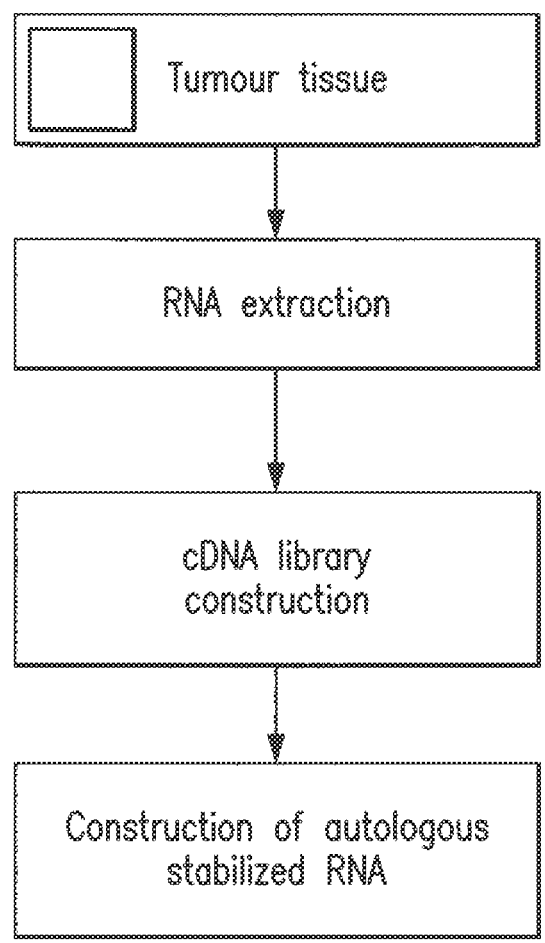
FIG. 10 shows a flow chart of the construction of autologous, stabilized RNA according to the preparation process of the present invention. Tumour tissue is first obtained, e.g. by biopsy. The total RNA is extracted from this. A cDNA library is constructed with the aid of the poly($A^+$) RNA obtained from the RNA extraction. Starting from this, after preparation of a corresponding DNA matrix, the autologous, stabilized RNA is obtained by means of in vitro transcription.

The aim is the preparation of autologous poly($A^+$) RNA. For this, poly($A^+$) RNA is isolated from the patient's own tumour tissue. This RNA isolated is very unstable per se and its amount is limited. The genetic information is therefore transcribed into a considerably more stable cDNA library and thus conserved. Starting from the patient's own cDNA library, stabilized autologous RNA can be prepared for the entire treatment period. The procedure according to the invention is shown schematically in FIG. 10.

Isolation of RNA

A process of Roche AG is used to isolate total RNA from a tumour tissue biopsy. The High Pure RNA Isolation Kit (order number 1828665) is employed here in accordance with the manufacturer's instructions. Poly($A^+$) RNA is isolated from the total RNA via a further process of Roche AG with the High Pure RNA Tissue Kit (order number 2033674).

Preparation of a cDNA Library

The cDNA library is constructed with the "SMART PCR cDNA Synthesis Kit" (Clontech Inc., USA; order number PT3041-1) in accordance with the manufacturer's instructions.

In this procedure, the single-stranded poly($A^+$) RNA is subjected to reverse transcription via a specific primer. Via a poly-C overhang at the 3'-end of the newly synthesized DNA, a further primer can hybridize, via which the construct can be amplified by a PCR. The double-stranded cDNA fragments are now ready for cloning into a suitable RNA production vector (e.g. pT7TS; cf. FIG. 8).

Figure 11:
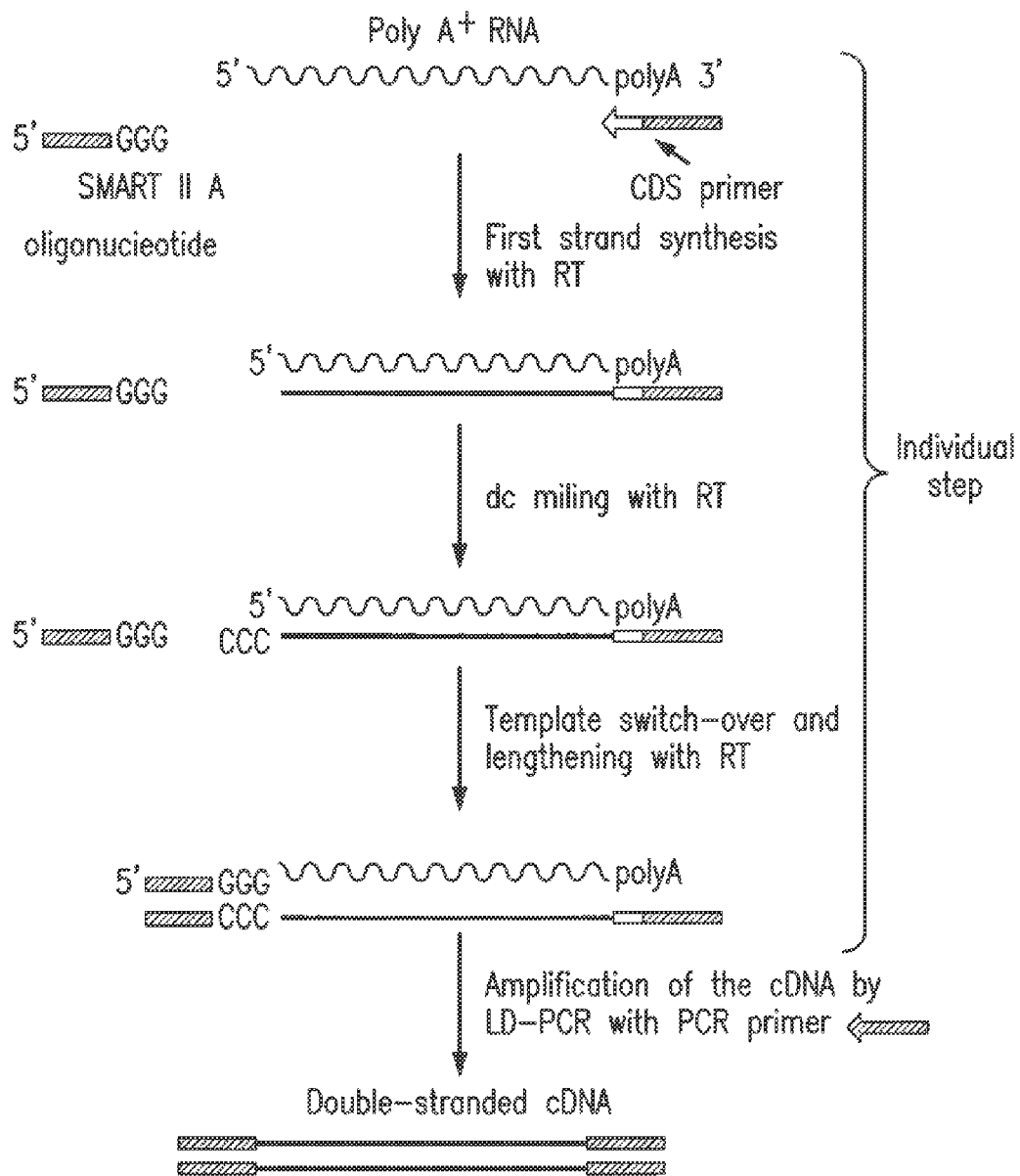
FIG. 11 shows a reaction scheme of the steps for preparation of a cDNA library, starting from poly($A^+$) RNA, for the SMART PCR cDNA Synthesis Kit from Clontech Inc. by way of example.

The process for the preparation of the cDNA library from the poly($A^+$) RNA with the aid of the above kit is shown schematically in FIG. 11.

Plasmid Constructs

Figure 12:
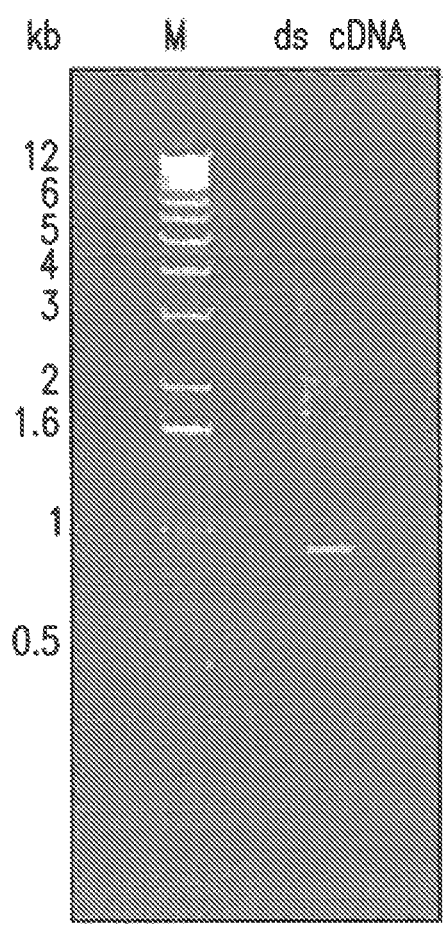
FIG. 12 shows a photograph of an agarose gel which shows the typical size fractionation of a cDNA library compiled from human placenta tissue. A length marker with fragments of the length shown on the left is plotted in track M. The "DS cDNA" track contains the cDNA library. Those fragments which correspond to the expected size fraction (about 200 bp to 4,000 bp) are used for the in vitro transcription.
Figure 14:
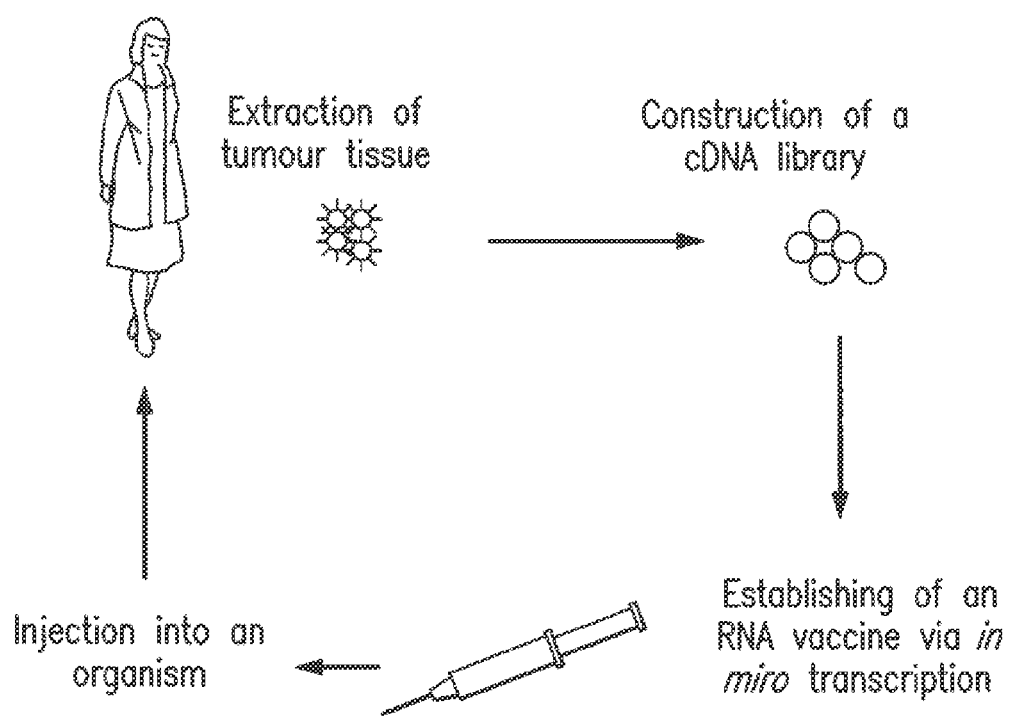
FIG. 14 shows once more schematically of the general course of a therapy with the pharmaceutical composition according to the invention with autologous, amplified tumour RNA, i.e. the RNA contained in the pharmaceutical composition represents a cDNA library of the tumour tissue. A sample of the tumour tissue is first obtained, e.g. via a biopsy. The total and then the poly($A^+$) RNA are prepared from the tissue by appropriate extractions. Starting from the poly($A^+$) RNA, a cDNA library is constructed and is cloned into a vector suitable for subsequent in vitro transcription. An RNA vaccine is then obtained by in vitro transcription, and is injected into the patient from whom the tumour tissue has been taken to combat the tumour.

The cDNA PCR fragments are cleaved with the restriction enzymes NotI and SpeI and cloned into the corresponding restriction sites of the pT7TS vector by a procedure analogous to that described in example 4. Plasmids of high purity are obtained via the Endo-free Maxipreparation Kit (Qiagen, Hilden, Germany). Plasmids with a cloned-in gene sequence which corresponds to the expected size fractionation (200 bp-4,000 bp) of the cDNA library are used for the in vitro transcription. An example of a separation of a representative cDNA library in an agarose gel is shown in FIG. 12.

In Vitro Transcription and RNA Administration

The in vitro transcription and the administration of the RNA are carried out as described in the above example 4.

Investigations During the Treatment

Before each inoculation (on the day of the inoculation):
Physical examination (including RR, fever);
Blood sample for routine laboratory values
1. Blood count, differential blood count: 3 ml
2. Electrolytes, LDH, CK, liver enzymes, bilirubin, creatinine, uric acid, total protein, CRP: 5 ml
3. Blood sedimentation: 2 ml; and
at repeat inoculations additionally: Inspection of the injection sites.
On day 1 after each inoculation:
Physical examination (including RR, fever); and
Inspection of the injection sites.
In staging analyses on day 56 and 126 after the first inoculation, then every 12 weeks, additionally:
Extended routine blood sample:
1. Tumour marker S 100 (7 ml)
2. Clotting values (3 ml);
Blood sample for immune monitoring (30 ml);
General well-being (ECOG score);
Imaging methods (thorax X-ray, sonography, skeleton scintigram, CT abdomen, pelvis, thorax, skull); and
ECG ("EKG").
Further Immunological Investigations In Vitro Where appropriate, the relative incidence of antigen-specific CTL precursor cells in the peripheral blood of the patient in the course of time of the vaccination therapy is measured.

On the one hand CTL precursor cells which are directed against antigens expressed to a particular degree by melanoma cells (tyrosinase, MAGE-3, melan-A, GP100) are quantified here with FACS analyses (tetramer staining). On the other hand ELIspot analyses are carried out, these being designed such that CTL precursor cells which are directed specifically against hitherto unknown antigens are additionally recorded. For this, autologous dendritic cells cultured from the peripheral blood of the patient are incubated with the same RNA with which the inoculation has also been carried out. These then serve as stimulator cells in the ELIspot analysis. The measurement thus records the total vaccine spectrum. For these analyses, blood samples of 30 ml in total (20 ml ELIspot, 10 ml FACS analysis) can be envisaged for the immune monitoring in the context of the staging analyses and additionally on days 0, 14, 28 and 42, as well as a single withdrawal of 100 ml on day 70 for culture of the DC.

Furthermore, skin biopsy samples from the injection site can be obtained for histological analysis in respect of a T cell infiltration.

Parameters for Evaluation of the Efficacy

The efficacy of the therapy according to the invention is evaluated with the aid of the parameters described above in example 4.

REFERENCES

Anichini, A, Mortarini, R., Maccalli, C., Squarcina, P., Fleishhauer, K., Mascheroni, L., Parmiani, G. (1996). Cytotoxic T cells directed to tumor antigens not expressed on normal melanocytes dominate HLA-A2.1-restricted immune repertoire to melanoma. J. Immunol. 156, 208-217.

Ashley, D M., Faiola, B., Nair, S., Hale, L P., Bigner, D D, Gilboa, E. (1997). Bone marrow-generated dendritic cells pulsed with tumor extracts or tumor RNA induce anti-tumor immunity against central nervous system tumors. J. Exp. Med. 186, 1177-1182.

Boczkowski, D., Nair, S K., Synder, D., Gilboa, E. (1996). Dendritic cells pulsed with RNA are potent antigen-presenting cells in vitro and in vivo. J. Exp. Med. 184, 465-472.

Boczkowski, D., Nair, S K., Nam, J., Lyerly, K., Gilboa, E. (2000). Induction of tumor immunity and cytotoxic T lymphocyte responses using dendritic cells transfected with messenger RNA amplified from tumor cells. Cancer Res. 60, 1028-1034.

Boon, T., Coulie, P., Marchand, M., Weynants, P., Wölfel, T., Brichard, V. (1994). Genes coding for tumor rejection antigens: perspectives for specific immunotherapy. In Important Advances in Oncology 1994. DeVita, V T, Hellman, S., Rosenberg, S A, ed. (Philadelphia: Lippincott Co), pp. 53-69.

Garbe, C, Orfanos, C E (1989): Epidemiologie des malignen Melanoms in der Bundesrepublik Deutschland im internationalen Vergleich [Epidemiology of malignant melanoma in the Federal Republic of Germany in an international comparison]. Onkologie 12, 253-262.

Grabbe, S., Bruvers, S., Gallo, R. L., Knisely, T. L., Nazareno, R., and Granstein, R. D. (1991). Tumor antigen presentation by murine epidermal cells. J Immunol. 146, 3656-3661.

Grabbe, S., Bruvers, S., Lindgren, A. M., Hosoi, J., Tan, K. C., and Granstein, R. D. (1992). Tumor antigen presentation by epidermal antigen-presenting cells in the mouse: modulation by granulocyte-macrophage colony-stimulating factor, tumor necrosis factor alpha, and ultraviolet radiation. J Leukoc. Biol. 52, 209-217.

Grabbe, S., Beissert, S., Schwarz, T., and Granstein, R. D. (1995). Dendritic cells as initiators of tumor immune responses: a possible strategy for tumor immunotherapy?. Immunol. Today 16, 117-121.

Grünebach, F, Müller, M R, Nencioni, A, Brugger, W, and Brossart, P (2002). Transfection of dendritic cells with RNA induces cytotoxic T lymphocytes against breast and renal cell carcinomas and reveals the immunodominance of presented T cell epitopes. submitted.

Heiser, A., Maurice, M A., Yancey, D R., Coleman, D M., Dahm, P., Vieweg, J. (2001). Human dendritic cells transfected with renal tumor RNA stimulate polyclonal T cell responses against antigens expressed by primary and metastatic tumors. Cancer Res. 61, 3388-3393.

Heiser, A., Maurice, M A., Yancey, D R., Wu, N Z., Dahm, P., Pruitt, S K., Boczkowski, D., Nair, S K., Ballo, M S., Gilboa, E., Vieweg, J. (2001). Induction of polyclonal prostate cancer-specific CTL using dendritic cells transfected with amplified tumor RNA. J. Immunol. 166, 2953-2960.

Hoerr, I, Obst, R, Rammensee, H G, Jung, G (2000). In vivo application of RNA leads to induction of specific cytotoxic T lymphocytes and antibodies. Eur J Immunol. 30, 1-7.

Houghton, A N (1994). Cancer antigens: immune recognition of self and altered self. J. Exp. Med 180, 1-4

Inaba, K, Young, J W and Steinman, R M (1987). Direct activation of CD8+ cytotoxic T lymphocytes by dendritic cells. J. Exp. Med. 166, 182-194.

Koido, S., Kashiwaba, M., Chen, D., Gendler, S., Kufe, D., Gong, J. (2000). Induction of antitumor immunity by vaccination of dendritic cells transfected with MUC1 RNA. J. Immunol. 165, 5713-5719.

Mitchell, D A., Nair, S K. (2000). RNA-transfected dendritic cells in cancer immunotherapy. J. Clin. Invest. 106, 1065-1069.

Nair, S., Boczkowski, S., Synder, D., Gilboa, E. (1998). Antigen presenting cells pulsed with unfractionated tumor-derived peptides are potent tumor vaccines. Eur. J. Immunol. 27, 589-597.

Nair, S., Heiser, A., Boczkowski, D., Majumdar, A., Naoe, M., Lebkowski, J S., Vieweg, J., Gilboa, E. (2000). Induction of cytotoxic T cell responses and tumor immunity against unrelated tumors using telomerase reverse transcriptase RNA transfected dendritic cells. Nat. Med. 6, 1011-1017.

Nestle, F. O., Alijagic, S., Gilliet, M., Sun, Y., Grabbe, S., Dummer, R., Burg, G., and Schadendorf, D. (1998). Vaccination of melanoma patients with peptide- or tumor lysate-pulsed dendritic cells. Nat. Med 4, 328-332.

Parkinson, D R, Houghton, A N, Hersey, P, Borden, E C (1992). Biologic therapy for melanoma. I Cutaneous melanoma. Balch, C M, Houghton, A N, Milton G W, Soober, A J, Soong, S J, ed. (Lippincott Co), pp. 522-541

Rammensee, H. G., Falk, K., and Rotzschke, O. (1993). Peptides naturally presented by MHC class I molecules. Annu. Rev. Immunol. 11, 213-244.

Romani N, Koide S, Crowley M, Witmer-Pack M, Livingstone A M, Fathman C G, Steinman R M: Presentation of exogenous protein antigens by dendritic cells to T cell clones. J Exp Med 169:1169, 1989.

Schadendorf, D, Grabbe, S, Nestle, F O (1997). Vaccination with Dendritic Cells—A specific Immunomodulatory Approach. In Strategies for Immunointervention in Dermatoilogy. Burg, G, Dummer, R G, ed. (Heidelberg, New York: Springer-Verlag), Schmitt, W E., Stassar, M J J G., Schmitt, W., Littlee, M., Cochlovius, B. (2001). In vitro induction of a bladder cancer-specific T-cell response by mRNA-transfected dendritic cells. J. Cancer Res. Clin. Oncol. 127, 203-206.

Schmoll H J, Höffken K, Possinger K (1997): Kompendium Internistische Onkologie [Compendium of Internal Oncology], 2nd ed., Springer-Verlag Berlin, part 2, 1415.

Schuler G and Steinmann R M (1985). Murine epidermal Langerhans cells mature into potent immunostimulatory dendritic cells in vitro. J. Exp. Med. 161, 526-546.

Thurner, B., Haendle, I., Roder, C. et al. (1999). Vaccination with Mage-3A1 peptide-pulsed mature, monocyte-derived dendritic cells expands specific cytotoxic T cells and induces regression of some metastases in advanced stage IV melanoma. J. Exp. Med. 190, 1669-1678.

The invention claimed is:

1. A method of stimulating an antitumor immune response in a subject comprising administering an effective amount of a cell-free composition comprising mRNA encoding an MAGE antigen to a subject in need thereof, thereby stimulating a T-cell mediated cytotoxic anticancer immune response in the subject.

2. The method of claim 1, wherein the subject has a cancer.

3. The method of claim 2, wherein the cancer is a lung or skin cancer.

4. The method of claim 1, wherein the composition comprises mRNA encoding at least 2, 3, 4 or 5 different tumor antigens.

5. The method of claim 1, wherein the method further comprises administering at least 2, 3, 4 or 5 different cell-free compositions comprising mRNA encoding different tumor antigens to the subject.

6. The method of claim 1, wherein the mRNA is complexed with at least one cationic or polycationic agent.

7. The method of claim 6, wherein the cationic or polycationic agent is chosen from the group consisting of protamine, poly-L-lysine, poly-L-arginine and histones.

8. The method of claim 7, wherein the mRNA is complexed with protamine.

9. The method of claim 1, further comprising administering one or more adjuvant(s) to the subject.

10. The method of claim 9, wherein the adjuvant is chosen from the group consisting of lipopolysaccharide, TNF-α, CD40 ligand, GP96, oligonucleotides with a CpG motif, aluminum hydroxide, Freund's adjuvant, a lipopeptide and a cytokine.

11. The method of claim 10, wherein the cytokine is GM-CSF.

12. The method of claim 1, wherein the mRNA encoding the antigen has a different nucleic acid sequence compared with the wild-type mRNA encoding the antigen.

13. The method of claim 1, wherein the mRNA comprises a 5' cap structure, at least one IRES and/or a poly(A$^+$) tail of at least 25 nucleotides.

14. The method of claim 13, wherein the mRNA comprises a 5' cap structure and a poly(A$^+$) tail of at least 25 nucleotides.

15. The method of claim 1, wherein the mRNA comprises at least one 5'-stabilizing sequence and/or at least one 3'-stabilizing sequence.

16. The method of claim 15, wherein the 5'- and/or the 3'-stabilizing sequence(s) is/are chosen from the group consisting of untranslated sequences (UTR) of the β-globin gene and a stabilizing sequence of the general formula (C/U)CCAN$_x$CCC(U/A)Py$_x$UC(C/U)CC.

17. The method of claim 1, wherein the mRNA comprises at least one analog of naturally occurring nucleotide selected from the group consisting of phosphorothioates, phosphoroamidates, peptide nucleotides, methylphosphates, 7-deazaguanosine, 5-methylcytosine and inosine.

18. The method of claim 1, wherein the cell-free composition comprising mRNA is administered by injection of an aqueous solution comprising the mRNA.

19. The method of claim 1, wherein the cell-free composition comprising mRNA is administered intradermally.

20. The method of claim 1, wherein the cell-free composition comprising mRNA is administered two or more times.

* * * * *

SEQUENCE LISTING

```
<160> NUMBER OF SEQ ID NOS: 4

<210> SEQ ID NO 1
<211> LENGTH: 22
<212> TYPE: RNA
<213> ORGANISM: Artificial Sequence
<220> FEATURE:
```

```
<223> OTHER INFORMATION: Synthetic stabilizing sequence
<220> FEATURE:
<221> NAME/KEY: modified_base
<222> LOCATION: (5)..(9)
<223> OTHER INFORMATION: a, c, u, g or absent
<220> FEATURE:
<221> NAME/KEY: misc_feature
<222> LOCATION: (5)..(9)
<223> OTHER INFORMATION: n is a, c, g, or u
<220> FEATURE:
<221> NAME/KEY: modified_base
<222> LOCATION: (14)..(17)
<223> OTHER INFORMATION: May or may not be present

<400> SEQUENCE: 1
yccannnnnc cwyyyyucy cc                                                  22

<210> SEQ ID NO 2
<211> LENGTH: 13
<212> TYPE: RNA
<213> ORGANISM: Artificial Sequence
<220> FEATURE:
<223> OTHER INFORMATION: Synthetic Kozak sequence

<400> SEQUENCE: 2
gccgccacca ugg                                                           13

<210> SEQ ID NO 3
<211> LENGTH: 45
<212> TYPE: DNA
<213> ORGANISM: Xenopus laevis

<400> SEQUENCE: 3
gcttgttctt tttgcagaag ctcagaataa acgctcaact ttggc                        45

<210> SEQ ID NO 4
<211> LENGTH: 157
<212> TYPE: DNA
<213> ORGANISM: Xenopus laevis

<400> SEQUENCE: 4
gactgactag gatctggtta ccactaaacc agcctcaaga acacccgaat ggagtctcta        60
agctacataa taccaactta cacttacaaa atgttgtccc ccaaaatgta gccattcgta       120
tctgctccta ataaaagaa agtttcttca cattcta                                 157
```